(12) United States Patent
Zhang

(10) Patent No.: US 9,469,846 B2
(45) Date of Patent: Oct. 18, 2016

(54) COMPOSITIONS AND METHODS FOR TREATING CANCER

(71) Applicant: Case Western Reserve University, Cleveland, OH (US)

(72) Inventor: Youwei Zhang, Beachwood, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 13/953,337

(22) Filed: Jul. 29, 2013

(65) Prior Publication Data

US 2014/0030245 A1    Jan. 30, 2014

Related U.S. Application Data

(60) Provisional application No. 61/676,596, filed on Jul. 27, 2012.

(51) Int. Cl.
*C12N 9/12* (2006.01)
*A61K 38/45* (2006.01)

(52) U.S. Cl.
CPC ............... *C12N 9/12* (2013.01); *A61K 38/45* (2013.01); *C12Y 207/11001* (2013.01)

(58) Field of Classification Search
CPC ............................ C12N 9/12; C12Q 1/6886
See application file for complete search history.

(56) References Cited

PUBLICATIONS

Pereira et al. 2009; Conserved ATRMec1 phosphorylation-independent activation of Chk1 by single amino acid substitution in the GD domain. Cell Cylce. 8(11): 1788-1793.*
Ng et al. 2004; Differential mode of regulation of the checkpoint kinases CHK1 and CHK2 by their regulatory domains . . . J. Biol. Chem. 279(10): 8808-8819.*
Wang et al. Aug. 1, 2012; Autoregulatory mechanisms of phosphorylation of checkpoint kinase 1. Cancer Rese. 72(15): 3786-3794.*
Matsuura et al. 2008; Cleavage-mediated activation of Chk1 during apoptosis. J. Biol. Chem. 283(37): 25485-25491.*

* cited by examiner

*Primary Examiner* — Karen Cochrane Carlson
(74) *Attorney, Agent, or Firm* — Tarolli, Sundheim, Covell & Tummino LLP

(57) ABSTRACT

A composition for inhibiting cancer cell proliferation includes exogenous constitutively active Chk1 or an agent that promotes phosphorylation of endogenous Chk1 of the cancer cell.

5 Claims, 10 Drawing Sheets

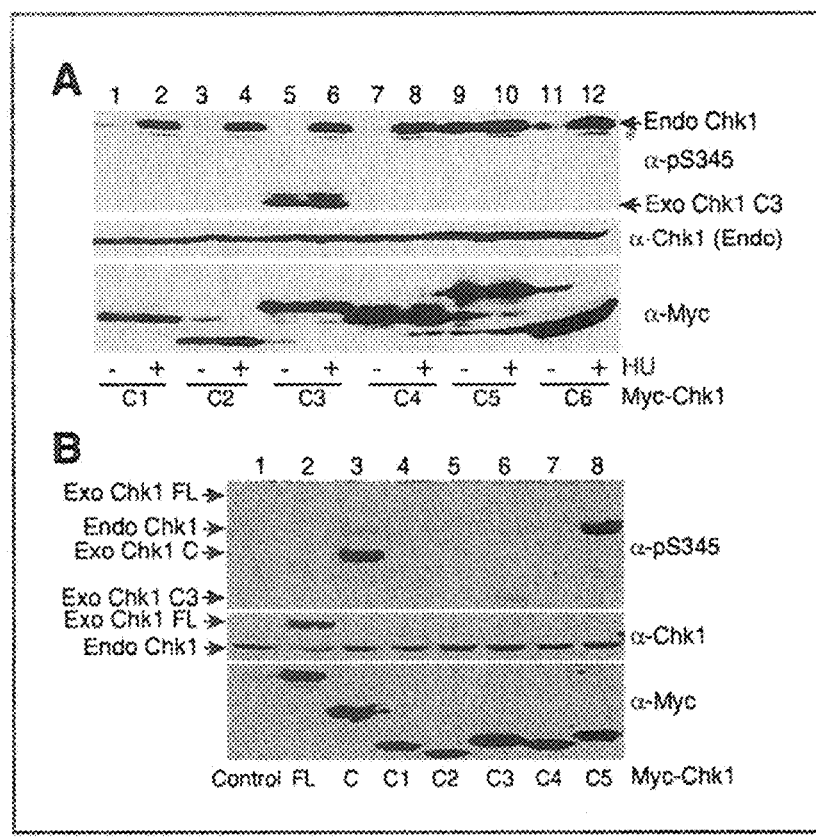
Figs. 4A-B
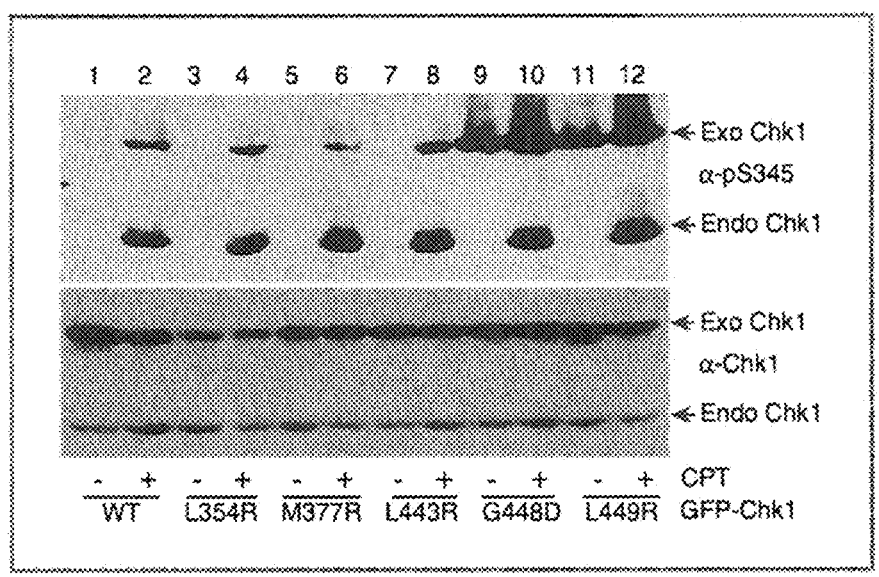
Fig. 5

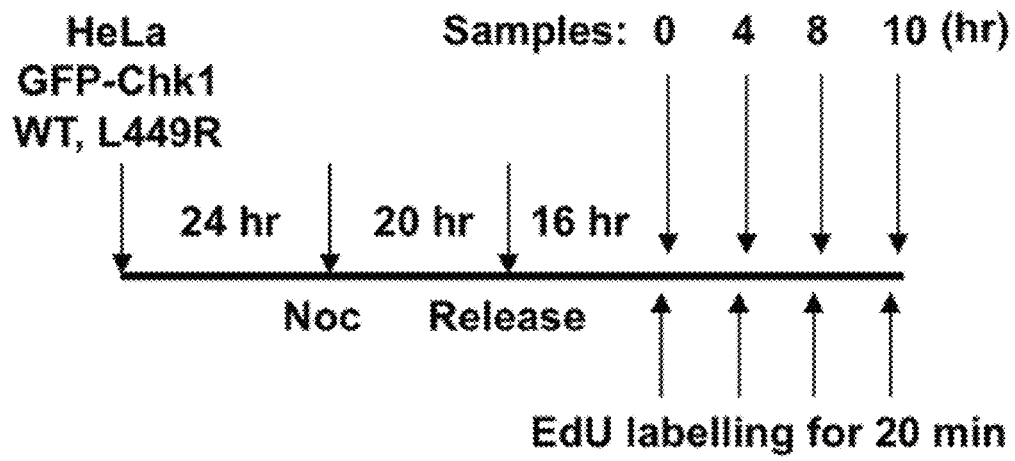
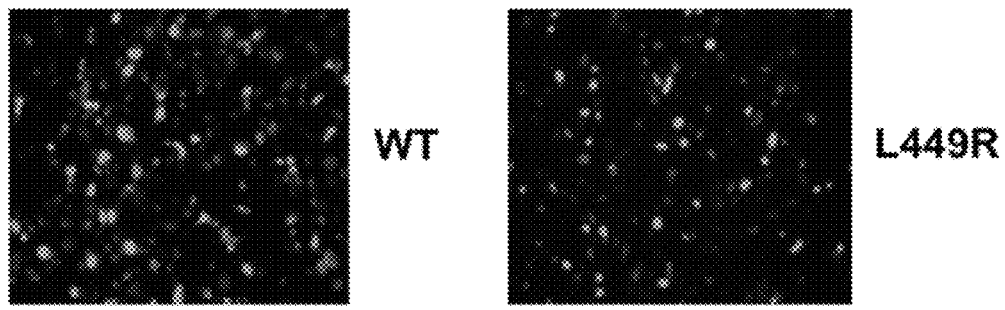
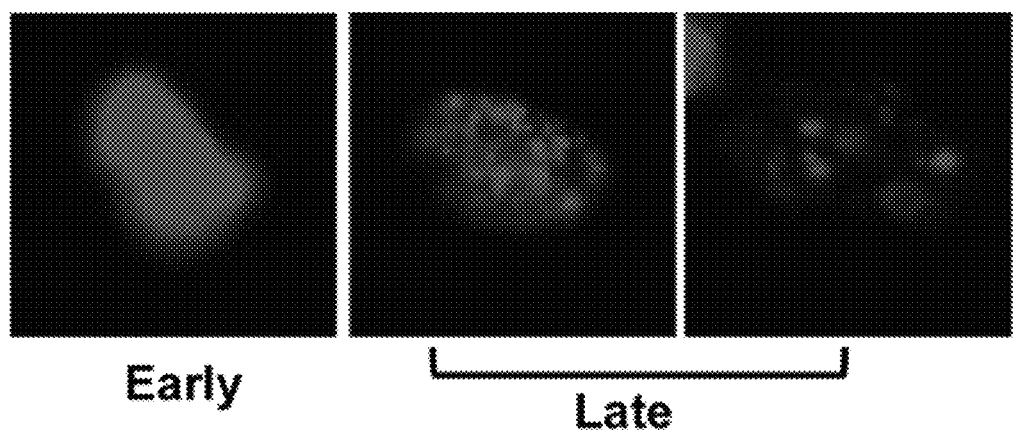
Figs. 11A-C

SEQUENCE LISTING

```
<160> NUMBER OF SEQ ID NOS: 5

<210> SEQ ID NO 1
<211> LENGTH: 476
<212> TYPE: PRT
<213> ORGANISM: Homo sapiens
<220> FEATURE:
<221> NAME/KEY: MOD_RES
<222> LOCATION: (317)..(317)
<223> OTHER INFORMATION: PHOSPHORYLATION
<220> FEATURE:
<221> NAME/KEY: MOD_RES
<222> LOCATION: (345)..(345)
<223> OTHER INFORMATION: PHOSPHORYLATION

<400> SEQUENCE: 1

Met Ala Val Pro Phe Val Glu Asp Trp Asp Leu Val Gln Thr Leu Gly
1               5                   10                  15

Glu Gly Ala Tyr Gly Glu Val Gln Leu Ala Val Asn Arg Val Thr Glu
            20                  25                  30

Glu Ala Val Ala Val Lys Ile Val Asp Met Lys Arg Ala Val Asp Cys
        35                  40                  45

Pro Glu Asn Ile Lys Lys Glu Ile Cys Ile Asn Lys Met Leu Asn His
    50                  55                  60

Glu Asn Val Val Lys Phe Tyr Gly His Arg Arg Glu Gly Asn Ile Gln
65                  70                  75                  80

Tyr Leu Phe Leu Glu Tyr Cys Ser Gly Gly Glu Leu Phe Asp Arg Ile
                85                  90                  95
```

Glu Pro Asp Ile Gly Met Pro Glu Pro Asp Ala Gln Arg Phe His
            100                 105                 110

Gln Leu Met Ala Gly Val Val Tyr Leu His Gly Ile Gly Ile Thr His
        115                 120                 125

Arg Asp Ile Lys Pro Glu Asn Leu Leu Leu Asp Glu Arg Asp Asn Leu
    130                 135                 140

Lys Ile Ser Asp Phe Gly Leu Ala Thr Val Phe Arg Tyr Asn Asn Arg
145                 150                 155                 160

Glu Arg Leu Leu Asn Lys Met Cys Gly Thr Leu Pro Tyr Val Ala Pro
                165                 170                 175

Glu Leu Leu Lys Arg Arg Glu Phe His Ala Glu Pro Val Asp Val Trp
            180                 185                 190

Ser Cys Gly Ile Val Leu Thr Ala Met Leu Ala Gly Glu Leu Pro Trp
        195                 200                 205

Asp Gln Pro Ser Asp Ser Cys Gln Glu Tyr Ser Asp Trp Lys Glu Lys
    210                 215                 220

Lys Thr Tyr Leu Asn Pro Trp Lys Lys Ile Asp Ser Ala Pro Leu Ala
225                 230                 235                 240

Leu Leu His Lys Ile Leu Val Glu Asn Pro Ser Ala Arg Ile Thr Ile
                245                 250                 255

Pro Asp Ile Lys Lys Asp Arg Trp Tyr Asn Lys Pro Leu Lys Lys Gly
            260                 265                 270

Ala Lys Arg Pro Arg Val Thr Ser Gly Gly Val Ser Glu Ser Pro Ser
        275                 280                 285

Gly Phe Ser Lys His Ile Gln Ser Asn Leu Asp Phe Ser Pro Val Asn
    290                 295                 300

Ser Ala Ser Ser Glu Glu Asn Val Lys Tyr Ser Ser Ser Gln Pro Glu
305                 310                 315                 320

Pro Arg Thr Gly Leu Ser Leu Trp Asp Thr Ser Pro Ser Tyr Ile Asp
                325                 330                 335

Lys Leu Val Gln Gly Ile Ser Phe Ser Gln Pro Thr Cys Pro Asp His
            340                 345                 350

Met Leu Leu Asn Ser Gln Leu Leu Gly Thr Pro Gly Ser Ser Gln Asn
        355                 360                 365

Pro Trp Gln Arg Leu Val Lys Arg Met Thr Arg Phe Phe Thr Lys Leu
    370                 375                 380

Asp Ala Asp Lys Ser Tyr Gln Cys Leu Lys Glu Thr Cys Glu Lys Leu
385                 390                 395                 400

Gly Tyr Gln Trp Lys Lys Ser Cys Met Asn Gln Val Thr Ile Ser Thr
                405                 410                 415

Thr Asp Arg Arg Asn Asn Lys Leu Ile Phe Lys Val Asn Leu Leu Glu
            420                 425                 430

Met Asp Asp Lys Ile Leu Val Asp Phe Arg Leu Ser Lys Gly Asp Gly
        435                 440                 445

Leu Glu Phe Lys Arg His Phe Leu Lys Ile Lys Gly Lys Leu Ile Asp
    450                 455                 460

Ile Val Ser Ser Gln Lys Val Trp Leu Pro Ala Thr
465                 470                 475

<210> SEQ ID NO 2
<211> LENGTH: 476
<212> TYPE: PRT
<213> ORGANISM: Homo sapiens

<400> SEQUENCE: 2

```
Met Ala Val Pro Phe Val Glu Asp Trp Asp Leu Val Gln Thr Leu Gly
1               5                   10                  15

Glu Gly Ala Tyr Gly Glu Val Gln Leu Ala Val Asn Arg Val Thr Glu
            20                  25                  30

Glu Ala Val Ala Val Lys Ile Val Asp Met Lys Arg Ala Val Asp Cys
        35                  40                  45

Pro Glu Asn Ile Lys Lys Glu Ile Cys Ile Asn Lys Met Leu Asn His
    50                  55                  60

Glu Asn Val Val Lys Phe Tyr Gly His Arg Arg Glu Gly Asn Ile Gln
65                  70                  75                  80

Tyr Leu Phe Leu Glu Tyr Cys Ser Gly Gly Glu Leu Phe Asp Arg Ile
                85                  90                  95

Glu Pro Asp Ile Gly Met Pro Glu Pro Asp Ala Gln Arg Phe Phe His
            100                 105                 110

Gln Leu Met Ala Gly Val Val Tyr Leu His Gly Ile Gly Ile Thr His
        115                 120                 125

Arg Asp Ile Lys Pro Glu Asn Leu Leu Leu Asp Glu Arg Asp Asn Leu
130                 135                 140

Lys Ile Ser Asp Phe Gly Leu Ala Thr Val Phe Arg Tyr Asn Asn Arg
145                 150                 155                 160

Glu Arg Leu Leu Asn Lys Met Cys Gly Thr Leu Pro Tyr Val Ala Pro
                165                 170                 175

Glu Leu Leu Lys Arg Arg Glu Phe His Ala Glu Pro Val Asp Val Trp
            180                 185                 190

Ser Cys Gly Ile Val Leu Thr Ala Met Leu Ala Gly Glu Leu Pro Trp
        195                 200                 205

Asp Gln Pro Ser Asp Ser Cys Gln Glu Tyr Ser Asp Trp Lys Glu Lys
210                 215                 220

Lys Thr Tyr Leu Asn Pro Trp Lys Lys Ile Asp Ser Ala Pro Leu Ala
225                 230                 235                 240

Leu Leu His Lys Ile Leu Val Glu Asn Pro Ser Ala Arg Ile Thr Ile
                245                 250                 255

Pro Asp Ile Lys Lys Asp Arg Trp Tyr Asn Lys Pro Leu Lys Lys Gly
            260                 265                 270

Ala Lys Arg Pro Arg Val Thr Ser Gly Gly Val Ser Glu Ser Pro Ser
        275                 280                 285

Gly Phe Ser Lys His Ile Gln Ser Asn Leu Asp Phe Ser Pro Val Asn
    290                 295                 300

Ser Ala Ser Ser Glu Glu Asn Val Lys Tyr Ser Ser Ser Gln Pro Glu
305                 310                 315                 320

Pro Arg Thr Gly Leu Ser Leu Trp Asp Thr Ser Pro Ser Tyr Ile Asp
                325                 330                 335

Lys Leu Val Gln Gly Ile Ser Phe Ser Gln Pro Thr Cys Pro Asp His
            340                 345                 350

Met Leu Leu Asn Ser Gln Leu Leu Gly Thr Pro Gly Ser Ser Gln Asn
        355                 360                 365

Pro Trp Gln Arg Leu Val Lys Arg Met Thr Arg Phe Phe Thr Lys Leu
    370                 375                 380

Asp Ala Asp Lys Ser Tyr Gln Cys Leu Lys Glu Thr Cys Glu Lys Leu
385                 390                 395                 400

Gly Tyr Gln Trp Lys Lys Ser Cys Met Asn Gln Val Thr Ile Ser Thr
                405                 410                 415
```

```
Thr Asp Arg Arg Asn Asn Lys Leu Ile Phe Lys Val Asn Leu Leu Glu
                420                 425                 430

Met Asp Asp Lys Ile Leu Val Asp Phe Arg Leu Ser Lys Gly Asp Gly
            435                 440                 445

Leu Glu Phe Lys Arg His Phe Leu Lys Ile Lys Gly Lys Leu Ile Asp
        450                 455                 460

Ile Val Ser Ser Gln Lys Val Trp Leu Pro Ala Thr
465                 470                 475

<210> SEQ ID NO 3
<211> LENGTH: 476
<212> TYPE: PRT
<213> ORGANISM: Homo sapiens

<400> SEQUENCE: 3

Met Ala Val Pro Phe Val Glu Asp Trp Asp Leu Val Gln Thr Leu Gly
1               5                   10                  15

Glu Gly Ala Tyr Gly Glu Val Gln Leu Ala Val Asn Arg Val Thr Glu
            20                  25                  30

Glu Ala Val Ala Val Lys Ile Val Asp Met Lys Arg Ala Val Asp Cys
        35                  40                  45

Pro Glu Asn Ile Lys Lys Glu Ile Cys Ile Asn Lys Met Leu Asn His
    50                  55                  60

Glu Asn Val Val Lys Phe Tyr Gly His Arg Arg Glu Gly Asn Ile Gln
65                  70                  75                  80

Tyr Leu Phe Leu Glu Tyr Cys Ser Gly Gly Glu Leu Phe Asp Arg Ile
                85                  90                  95

Glu Pro Asp Ile Gly Met Pro Glu Pro Asp Ala Gln Arg Phe Phe His
            100                 105                 110

Gln Leu Met Ala Gly Val Val Tyr Leu His Gly Ile Gly Ile Thr His
        115                 120                 125

Arg Asp Ile Lys Pro Glu Asn Leu Leu Leu Asp Glu Arg Asp Asn Leu
    130                 135                 140

Lys Ile Ser Asp Phe Gly Leu Ala Thr Val Phe Arg Tyr Asn Asn Arg
145                 150                 155                 160

Glu Arg Leu Leu Asn Lys Met Cys Gly Thr Leu Pro Tyr Val Ala Pro
                165                 170                 175

Glu Leu Leu Lys Arg Arg Glu Phe His Ala Glu Pro Val Asp Val Trp
            180                 185                 190

Ser Cys Gly Ile Val Leu Thr Ala Met Leu Ala Gly Glu Leu Pro Trp
        195                 200                 205

Asp Gln Pro Ser Asp Ser Cys Gln Glu Tyr Ser Asp Trp Lys Glu Lys
    210                 215                 220

Lys Thr Tyr Leu Asn Pro Trp Lys Lys Ile Asp Ser Ala Pro Leu Ala
225                 230                 235                 240

Leu Leu His Lys Ile Leu Val Glu Asn Pro Ser Ala Arg Ile Thr Ile
                245                 250                 255

Pro Asp Ile Lys Lys Asp Arg Trp Tyr Asn Lys Pro Leu Lys Lys Gly
            260                 265                 270

Ala Lys Arg Pro Arg Val Thr Ser Gly Gly Val Ser Glu Ser Pro Ser
        275                 280                 285

Gly Phe Ser Lys His Ile Gln Ser Asn Leu Asp Phe Ser Pro Val Asn
    290                 295                 300
```

-continued

Ser Ala Ser Ser Glu Glu Asn Val Lys Tyr Ser Ser Gln Pro Glu
305                 310                 315                 320

Pro Arg Thr Gly Leu Ser Leu Trp Asp Thr Ser Pro Ser Tyr Ile Asp
                325                 330                 335

Lys Leu Val Gln Gly Ile Ser Phe Ser Gln Pro Thr Cys Pro Asp His
            340                 345                 350

Met Leu Leu Asn Ser Gln Leu Leu Gly Thr Pro Gly Ser Ser Gln Asn
        355                 360                 365

Pro Trp Gln Arg Leu Val Lys Arg Met Thr Arg Phe Phe Thr Lys Leu
    370                 375                 380

Asp Ala Asp Lys Ser Tyr Gln Cys Leu Lys Glu Thr Cys Glu Lys Leu
385                 390                 395                 400

Gly Tyr Gln Trp Lys Lys Ser Cys Met Asn Gln Val Thr Ile Ser Thr
                405                 410                 415

Thr Asp Arg Arg Asn Asn Lys Leu Ile Phe Lys Val Asn Leu Leu Glu
            420                 425                 430

Met Asp Asp Lys Ile Leu Val Asp Phe Arg Leu Ser Lys Gly Asp Gly
        435                 440                 445

Arg Glu Phe Lys Arg His Phe Leu Lys Ile Lys Gly Lys Leu Ile Asp
    450                 455                 460

Ile Val Ser Ser Gln Lys Val Trp Leu Pro Ala Thr
465                 470                 475

<210> SEQ ID NO 4
<211> LENGTH: 146
<212> TYPE: PRT
<213> ORGANISM: Homo sapiens

<400> SEQUENCE: 4

Ser Pro Ser Tyr Ile Asp Lys Leu Val Gln Gly Ile Ser Phe Ser Gln
1               5                   10                  15

Pro Thr Cys Pro Asp His Met Leu Leu Asn Ser Gln Leu Leu Gly Thr
            20                  25                  30

Pro Gly Ser Ser Gln Asn Pro Trp Gln Arg Leu Val Lys Arg Met Thr
        35                  40                  45

Arg Phe Phe Thr Lys Leu Asp Ala Asp Lys Ser Tyr Gln Cys Leu Lys
    50                  55                  60

Glu Thr Cys Glu Lys Leu Gly Tyr Gln Trp Lys Lys Ser Cys Met Asn
65                  70                  75                  80

Gln Val Thr Ile Ser Thr Thr Asp Arg Arg Asn Asn Lys Leu Ile Phe
                85                  90                  95

Lys Val Asn Leu Leu Glu Met Asp Asp Lys Ile Leu Val Asp Phe Arg
            100                 105                 110

Leu Ser Lys Gly Asp Gly Leu Glu Phe Lys Arg His Phe Leu Lys Ile
        115                 120                 125

Lys Gly Lys Leu Ile Asp Ile Val Ser Ser Gln Lys Val Trp Leu Pro
    130                 135                 140

Ala Thr
145

<210> SEQ ID NO 5
<211> LENGTH: 56
<212> TYPE: PRT
<213> ORGANISM: Homo sapiens

```
<400> SEQUENCE: 5

Asn Asn Lys Leu Ile Phe Lys Val Asn Leu Leu Glu Met Asp Asp Lys
1               5                   10                  15

Ile Leu Val Asp Phe Arg Leu Ser Lys Gly Asp Gly Leu Glu Phe Lys
                20                  25                  30

Arg His Phe Leu Lys Ile Lys Gly Lys Leu Ile Asp Ile Val Ser Ser
            35                  40                  45

Gln Lys Val Trp Leu Pro Ala Thr
    50                  55
```

US 9,469,846 B2

COMPOSITIONS AND METHODS FOR TREATING CANCER

RELATED APPLICATION

This application claims priority from U.S. Provisional Application No. 61/676,596, filed Jul. 27, 2012, the subject matter of which is incorporated herein by reference in its entirety.

BACKGROUND

Cells activate genome surveillance pathways, called cell-cycle checkpoints in response to replication perturbation or DNA damage. Central to these surveillance pathways are protein kinases, the upstream kinase, ATR (ataxia telangiectasia mutated and Rad3 related), and its downstream target kinase, Chk1 (checkpoint kinase 1). Complete loss of CHK1 or ATR leads to embryonic lethality in mice. On the other hand, partial loss of these genes, for instance loss of one copy of CHKI or a hypomorphic mutation in ATR, increased genome instability and caused spontaneous cell death even in the absence of extrinsic stress. These findings suggest that these two proteins play key roles in monitoring the DNA replication and in maintaining the genome integrity.

SUMMARY

Embodiments described herein relate to compositions and methods for inhibiting cancer cell proliferation. The composition can include exogenous constitutively active Chk1 or an agent that promotes phosphorylation of endogenous Chk1 of a cancer cell.

In some embodiments, the constitutively active Chk1 can include Chk1 that is phosphorylated after administration to or expression in the cancer cell. In other embodiments, the constitutively active Chk1 can include an L449R mutant of Chk1 that is phoshporylated after administration to or expression in the cancer cell.

In some embodiments, the agent can include a small molecule or polypeptide that inhibits the interaction of the N-terminal kinase domain and the C-terminal kinase domain of the endogenous Chk1. The agent can include, for example, a polypeptide that has an amino acid sequence with at least 80% sequence identity to amino acids 331-476 of Chk1 or amino acids 421-476 of Chk1.

Other embodiments described herein relate to a method for inhibiting cancer cell proliferation. The method includes administering to the cancer cell a therapeutically effective amount of constitutively active Chk1 or an agent that promotes phosphorylation of endogenous Chk1 of the cancer cell.

In some embodiments, the constitutively active Chk1 can include Chk1 that is phosphorylated after administration to or expression in the cancer cell. In other embodiments, the constitutively active Chk1 can include an L449R mutant of Chk1 that is phoshporylated after administration to or expression in the cancer cell.

In some embodiments, the agent can include a small molecule or polypeptide that inhibits the interaction of the N-terminal kinase domain and the C-terminal kinase domain of the endogenous Chk1. The agent can include a polypeptide that has a amino acid sequence with at least 80% sequence identity to amino acids 331-476 of Chk1 or amino acids 421-476 of Chk1.

BRIEF DESCRIPTION OF THE DRAWINGS

FIG. 4 illustrates constitutive phosphorylation of endogenous Chk1. A, HEK293T cells were transfected with Myc-tagged Chk1 C-terminal fragments for 48 hours. treated or not with 2 mmol/L hydroxyurea (HU) for 1 hour, and immunoblotted with indicated antibodies. The asterisk indicates a non-Chk1 protein cross-reacted with the anti-p-Ser-345 antibodies after HU treatment. B, HeLa cells were transfected with Myc-tagged Chk1 FL or truncated mutants for 48 hours and immunoblotted with indicated antibodies. Overexpressed (Exo) and endogenous (Endo) Chk1 proteins were shown by arrows.

FIG. 5 illustrates the roles of the CM2 domain in Chk1 phosphorylation. HEK293T cells were transfected with GFP-tagged full-length Chk1 WT or point mutants for 48 hours, treated or not with 500 nmol/L CPT for 2 hours, and immunoblotted with indicated antibodies. Overexpressed (Exo) and endogenous (Endo) Chk1 proteins are shown by arrows.

Figure 7:
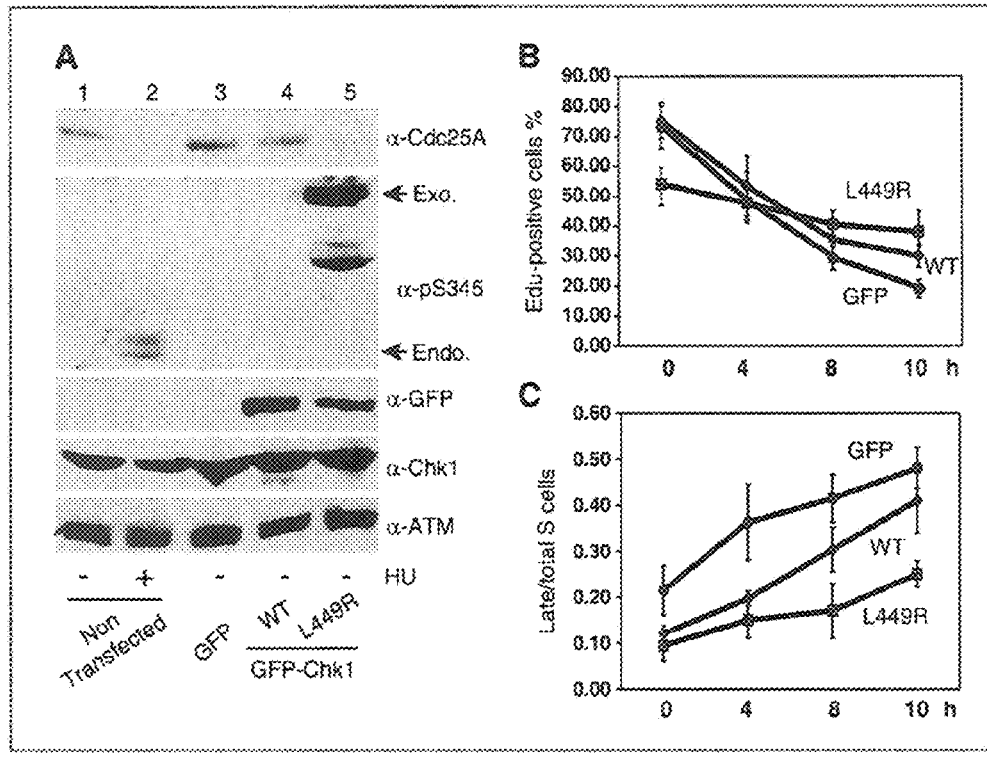

FIG. 7 illustrates the checkpoint activation by constitutive phosphorylation of Chk1. A, HeLa Tet/Off cells were transfected or not with tetracycline-inducible GFP, GFP-Chk1 WT, or the L449R mutant for 48 hours in the absence of doxycycline, treated or not with 2 mmol/L HU for 1 hour, and immunoblotted with indicated antibodies. B, HeLa Tet/Off cells were transfected with tetracycline-inducible GFP, GFP-Chk1 WT, or the L449R mutant and cultured in the presence of 1 mg/mL doxycycline for 24 hours, synchronized at the $G_2/M$ phase by 100 ng/mL nocodazole for 20 hours, released into doxycycline-free medium for 16 hours, and then chased for additional 0, 4, 8, or 10 hours. During the last 20 minutes of each chase period, cells were labeled with 10 μmol/L EdU, fixed, and analyzed as described in Materials and Methods. Data represent mean and SD of EdU-positive cells from 3 independent experiments. C, EdU-positive cells from B were further divided into late versus early S phase as shown in Supplementary FIG. S3C. The ratio of late versus total S-phase cells was measured. Data represent mean and SD from 3 independent experiments.

Figure 8:
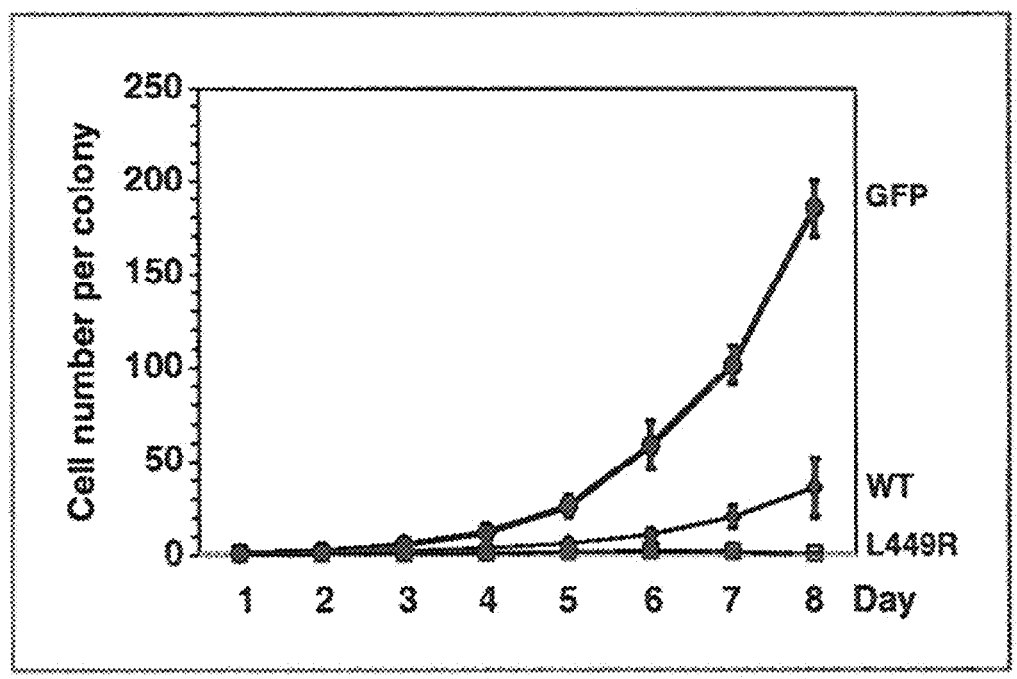

FIG. 8 illustrates growth suppression by constitutively active Chk1. HEK293T cells plated in 12-well plates were transfected with vectors expressing GFP, GFP-Chk1 WT, or GFP-Chk1 L449R mutant for 48 hours. The cells were reseeded into 6-well plates in triplicate at a density of 10,000 cells per well, cultured for 1 to 8 days. On each day, the number of GFP positive cells within each colony was counted under fluorescence microscope. Data represent mean and SD from 3 independent experiments.

Figure 9A:
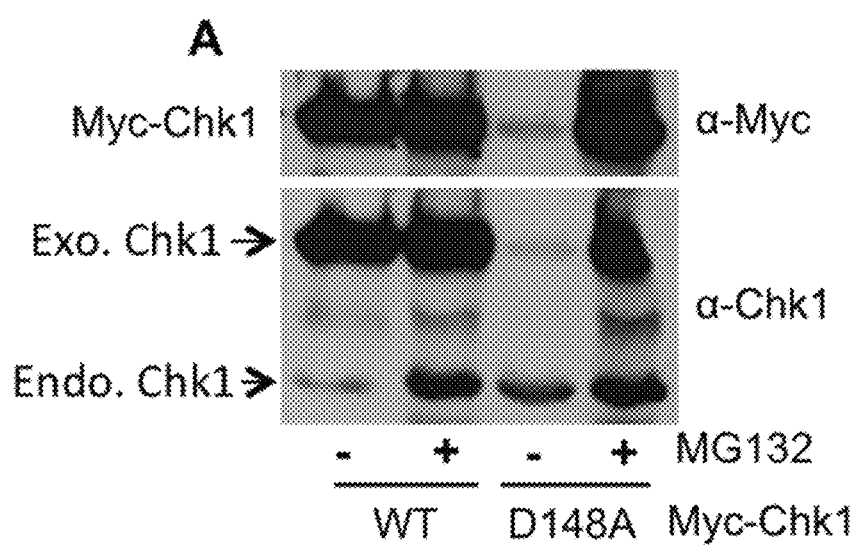
Figure 9B:
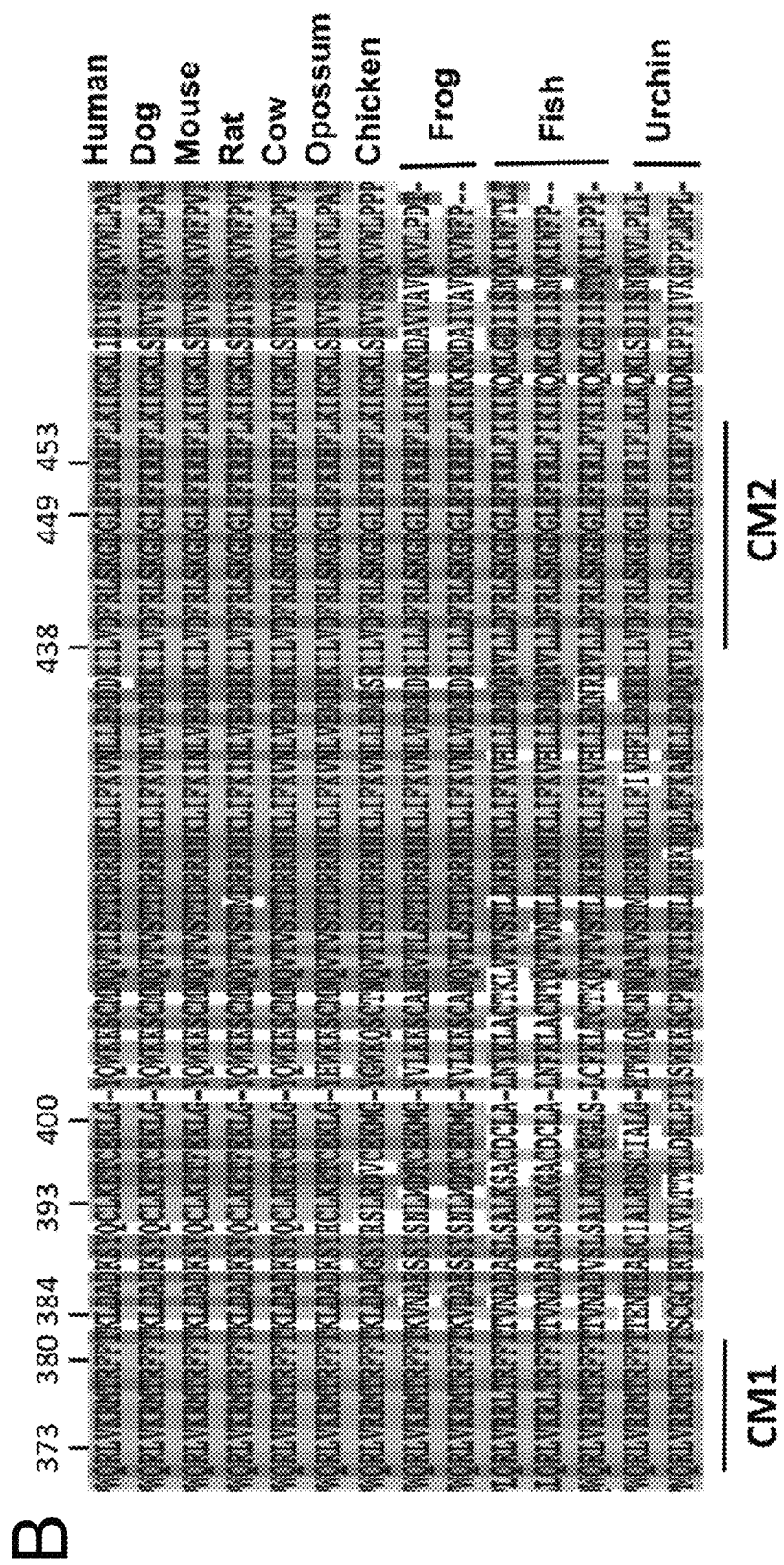

FIG. 9 illustrates, (A) HEK293T cells were transfected with Myc-Chk1 WT or D148A mutant for 48 hr, treated with 2 μM MG132 for additional 12 hr, and immunoblotted with indicated antibodies. Exogenous (Exo) and endogenous (Endo) Chk1 proteins are shown by arrows. (B) Alignment of the domain from CM1 to the distal C-terminus of Chk1 from different species. Conserved residues are listed.

FIG. 10 illustrates (A) HEK293T cells were transfected with Myc-tagged Chk1 FL, N- or C-terminal fragments for 48 hr, immunoblotted with indicated antibodies. Endogenous (endo) and exogenous (exo) Chk1 proteins are shown by arrows. The anti-Chk1 antibody (G4 from Santa Cruz) also recognized the N-terminal kinase domain, but not the C-terminal domain of Chk1. (B) Schematic diagram of generating GFP-tagged Chk1 C-terminal fragments. (C) HEK293T cells were transfected with Myc-Chk1 N-terminus and GFP-tagged Chk1 C-terminal fragments for 48 hr, immunoprecipitated with anti-Myc antibodies and immunoblotted with anti-GFP antibodies. Whole cell extracts (WCE) were also blotted. (D) Myc-Chk1 WT or L449R mutant proteins were produced by in vitro transcription and translation, and used to perform in vitro kinase assay with the GST-Cdc25C (200-256) as the substrate. Note the strong auto-phosphorylation of the L449R mutant.

FIG. 11 illustrates constitutive activation of Chk1 inhibits S phase progression. (A) Schematic diagram of experimental design. Samples were collected after a 16-hr release from nocodazole (Noc) block. EdU (10 μM) was added 20 min before each chase time point. (B) Protein expression of GFP-Chk1 WT or L449R mutant 16 hr after the nocodazole release. (e) Typical EdU staining for early versus late S phase cells.

DETAILED DESCRIPTION

The present invention is not limited to the particular methodology, protocols, and reagents, etc., described herein and as such may vary. The terminology used herein is for the purpose of describing particular embodiments only, and is not intended to limit the scope of the present invention, which is defined solely by the claims. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and does not constitute any admission as to the correctness of the dates or contents of these documents.

Unless otherwise defined, scientific and technical terms used herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art.

As used herein, "one or more of a, b, and c" means a, b, c, ab, ac, bc, or abc. The use of "or" herein is the inclusive or.

As used herein, the term "administering" to a patient includes dispensing, delivering or applying an active compound in a pharmaceutical formulation to a subject by any suitable route for delivery of the active compound to the desired location in the subject (e.g., to thereby contact a desired cell such as a desired epithelial cell), including administration into the cerebrospinal fluid or across the blood-brain barrier, delivery by either the parenteral or oral route, intramuscular injection, subcutaneous or intradermal injection, intravenous injection, buccal administration, transdermal delivery and administration by the rectal, colonic, vaginal, intranasal or respiratory tract route. The compositions or agents may, for example, be administered to a comatose, anesthetized or paralyzed subject via an intravenous injection or may be administered intravenously to a pregnant subject to stimulate axonal growth in a fetus. Specific routes of administration may include topical application, such as by eyedrops, creams or erodible formulations to be placed under the eyelid, intraocular injection into the aqueous or the vitreous humor, injection into the external layers of the eye, such as via subconjunctival injection or subtenon injection, parenteral administration or via oral routes.

As used herein, a "chimeric protein" or "fusion protein" is a fusion of a first amino acid sequence encoding a polypeptide with a second amino acid sequence defining a domain (e.g., polypeptide portion) foreign to and not substantially homologous with the domain of the first polypeptide. A chimeric protein may present a foreign domain, which is found (albeit in a different protein) in an organism, which also expresses the first protein, or it may be an "interspecies", "intergenic", etc. fusion of protein structures expressed by different kinds of organisms.

As used herein, the term "contacting cell" or "treating cells" refers to any mode of agent delivery or "administration," either to cells or to whole organisms, in which the agent is capable of exhibiting its pharmacological effect in the cells. "Contacting cells" includes both in vivo and in vitro methods of bringing an agent of the invention into proximity with a neuron. Suitable modes of administration can be determined by those skilled in the art and such modes of administration may vary between agents. For example, when cancer cells are treated, agents can be administered, for example, by transfection, lipofection, electroporation, viral vector infection, or by addition to growth medium.

As used herein an "effective amount" of an agent or therapeutic polypeptide is an amount sufficient to achieve a desired therapeutic or pharmacological effect, such as an amount that is capable of activating the growth of neurons. An effective amount of an agent as defined herein may vary according to factors such as the disease state, age, and weight of the subject, and the ability of the agent to elicit a desired response in the subject. Dosage regimens may be adjusted to provide the optimum therapeutic response. An effective amount is also one in which any toxic or detrimental effects of the active compound are outweighed by the therapeutically beneficial effects.

As used herein, the term a "therapeutically effective amount" refers to an amount effective, at dosages and for periods of time necessary, to achieve the desired therapeutic result. A therapeutic result may be, e.g., lessening of symptoms, prolonged survival, improved mobility, and the like. A therapeutic result need not be a "cure."

As used herein, the term "expression" refers to the process by which nucleic acid is translated into peptides or is transcribed into RNA, which, for example, can be translated into peptides, polypeptides or proteins. If the nucleic acid is derived from genomic DNA, expression may, if an appropriate eukaryotic host cell or organism is selected, include splicing of the mRNA. For heterologous nucleic acid to be expressed in a host cell, it must initially be delivered into the cell and then, once in the cell, ultimately reside in the nucleus.

As used herein, the term "genetic therapy" involves the transfer of heterologous DNA to cells of a mammal, particularly a human, with a disorder or conditions for which therapy or diagnosis is sought. The DNA is introduced into the selected target cells in a manner such that the heterologous DNA is expressed and a therapeutic product encoded thereby is produced. Alternatively, the heterologous DNA may in some manner mediate expression of DNA that encodes the therapeutic product; it may encode a product, such as a peptide or RNA that in some manner mediates, directly or indirectly, expression of a therapeutic product. Genetic therapy may also be used to deliver nucleic acid encoding a gene product to replace a defective gene or supplement a gene product produced by the mammal or the cell in which it is introduced. The introduced nucleic acid may encode a therapeutic compound, such as a growth factor inhibitor thereof, or a tumor necrosis factor or inhibitor thereof, such as a receptor therefore, that is not normally produced in the mammalian host or that is not produced in therapeutically effective amounts or at a therapeutically useful time. The heterologous DNA encoding the therapeutic product may be modified prior to introduction into the cells of the afflicted host in order to enhance or otherwise alter the product or expression thereof.

As used herein, the term "gene" or "recombinant gene" refers to a nucleic acid comprising an open reading frame encoding a polypeptide, including both exon and (optionally) intron sequences.

As used herein, the term "heterologous nucleic acid sequence" is typically DNA that encodes RNA and proteins that are not normally produced in vivo by the cell in which it is expressed or that mediates or encodes mediators that alter expression of endogenous DNA by affecting transcription, translation, or other regulatable biochemical processes. A heterologous nucleic acid sequence may also be referred to as foreign DNA. Any DNA that one of skill in the art would recognize or consider as heterologous or foreign to the cell in which it is expressed is herein encompassed by heterologous DNA. Antibodies that are encoded by heterologous DNA may be secreted or expressed on the surface of the cell in which the heterologous DNA has been introduced.

As use herein, the terms "homology" and "identity" are used synonymously throughout and refer to sequence similarity between two peptides or between two nucleic acid molecules. Homology can be determined by comparing a position in each sequence, which may be aligned for purposes of comparison. When a position in the compared sequence is occupied by the same base or amino acid, then the molecules are homologous or identical at that position. A degree of homology or identity between sequences is a function of the number of matching or homologous positions shared by the sequences.

As used herein, the phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, subcapsular, subarachnoid, intraspinal and intrasternal injection and infusion.

As used herein, the phrases "systemic administration," "administered systemically," "peripheral administration" and "administered peripherally" as used herein mean the administration of a compound, drug or other material other than directly into a target tissue (e.g., the tumor), such that it enters the animal's system and, thus, is subject to metabolism and other like processes, for example, subcutaneous administration.

As use herein, the term "patient" or "subject" or "animal" or "host" refers to any mammal. The subject may be a human, but can also be a mammal in need of veterinary treatment, e.g., domestic animals (e.g., dogs, cats, and the like), farm animals (e.g., cows, sheep, fowl, pigs, horses, and the like) and laboratory animals (e.g., rats, mice, guinea pigs, and the like).

As used herein, the terms "polynucleotide sequence" and "nucleotide sequence" are also used interchangeably herein.

As used herein, the terms "peptide" or "polypeptide" are used interchangeably herein and refer to compounds consisting of from about 2 to about 90 amino acid residues, inclusive, wherein the amino group of one amino acid is linked to the carboxyl group of another amino acid by a peptide bond. A peptide can be, for example, derived or removed from a native protein by enzymatic or chemical cleavage, or can be prepared using conventional peptide synthesis techniques (e.g., solid phase synthesis) or molecular biology techniques (see Sambrook et al., MOLECULAR CLONING: LAB. MANUAL (Cold Spring Harbor Press, Cold Spring Harbor, N.Y., 1989)). A "peptide" can comprise any suitable L- and/or D-amino acid, for example, common a-amino acids (e.g., alanine, glycine, valine), non-a-amino acids (e.g., P-alanine, 4-aminobutyric acid, 6aminocaproic acid, sarcosine, statine), and unusual amino acids (e.g., citrulline, homocitruline, homoserine, norleucine, norvaline, ornithine). The amino, carboxyl and/or other functional groups on a peptide can be free (e.g., unmodified) or protected with a suitable protecting group. Suitable protecting groups for amino and carboxyl groups, and means for adding or removing protecting groups are known in the art. See, e.g., Green & Wuts, PROTECTING GROUPS IN ORGANIC SYNTHESIS (John Wiley & amp; Sons, 1991). The functional groups of a peptide can also be derivatized (e.g., alkylated) using art-known methods.

As used herein, the term "peptidomimetic", refers to a protein-like molecule designed to mimic a peptide. Peptidomimetics typically arise either from modification of an existing peptide, or by designing similar systems that mimic peptides, such as peptoids and β-peptides. Irrespective of the approach, the altered chemical structure is designed to advantageously adjust the molecular properties, such as stability or biological activity. These modifications involve changes to the peptide that do not occur naturally (such as altered backbones and the incorporation of nonnatural amino acids).

A polynucleotide sequence (DNA, RNA) is "operatively linked" to an expression control sequence when the expression control sequence controls and regulates the transcription and translation of that polynucleotide sequence. The term "operatively linked" includes having an appropriate start signal (e.g., ATG) in front of the polynucleotide sequence to be expressed, and maintaining the correct reading frame to permit expression of the polynucleotide sequence under the control of the expression control sequence, and production of the desired polypeptide encoded by the polynucleotide sequence.

As used herein, the term "recombinant," as used herein, means that a protein is derived from a prokaryotic or eukaryotic expression system.

As used herein, the term "tissue-specific promoter" means a nucleic acid sequence that serves as a promoter, i.e., regulates expression of a selected nucleic acid sequence operably linked to the promoter, and which affects expression of the selected nucleic acid sequence in specific cells of a tissue. The term also covers so-called "leaky" promoters, which regulate expression of a selected nucleic acid primarily in one tissue, but cause expression in other tissues as well. The term "transfection" is used to refer to the uptake of foreign DNA by a cell. A cell has been "transfected" when exogenous DNA has been introduced inside the cell membrane. A number of transfection techniques are generally known in the art. See, e.g., Graham et al., Virology 52:456 (1973); Sambrook et al., Molecular Cloning: A Laboratory Manual (1989); Davis et al., Basic Methods in Molecular Biology (1986); Chu et al., Gene 13:197 (1981). Such techniques can be used to introduce one or more exogenous DNA moieties, such as a nucleotide integration vector and other nucleic acid molecules, into suitable host cells. The term captures chemical, electrical, and viral-mediated transfection procedures.

As used herein, the terms "transcriptional regulatory sequence" is a generic term used throughout the specification to refer to nucleic acid sequences, such as initiation signals, enhancers, and promoters, which induce or control transcription of protein coding sequences with which they are operably linked. In some examples, transcription of a recombinant gene is under the control of a promoter sequence (or other transcriptional regulatory sequence), which controls the expression of the recombinant gene in a cell-type in which expression is intended. It will also be understood that the recombinant gene can be under the control of transcriptional regulatory sequences which are the same or which are different from those sequences, which control transcription of the naturally occurring form of a protein.

As used herein, the term "vector" refers to a nucleic acid molecule capable of transporting another nucleic acid to which it has been linked. Preferred vectors are those capable of one or more of, autonomous replication and expression of nucleic acids to which they are linked. Vectors capable of directing the expression of genes to which they are operatively linked are referred to herein as "expression vectors".

As used herein, the term "wild type" refers to the naturally-occurring polynucleotide sequence encoding a protein, or a portion thereof, or protein sequence, or portion thereof, respectively, as it normally exists in vivo. As used herein, the term "nucleic acid" refers to polynucleotides, such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

The agents, compounds, compositions, antibodies, etc. used in the methods described herein are considered to be purified and/or isolated prior to their use. Purified materials are typically "substantially pure", meaning that a nucleic acid, polypeptide or fragment thereof, or other molecule has been separated from the components that naturally accompany it. Typically, the polypeptide is substantially pure when it is at least 60%, 70%, 80%, 90%, 95%, or even 99%, by weight, free from the proteins and other organic molecules with which it is associated naturally. For example, a substantially pure polypeptide may be obtained by extraction from a natural source, by expression of a recombinant nucleic acid in a cell that does not normally express that protein, or by chemical synthesis. "Isolated materials" have been removed from their natural location and environment. In the case of an isolated or purified domain or protein fragment, the domain or fragment is substantially free from amino acid sequences that flank the protein in the naturally-occurring sequence. The term "isolated DNA" means DNA has been substantially freed of the genes that flank the given DNA in the naturally occurring genome. Thus, the term "isolated DNA" encompasses, for example, cDNA, cloned genomic DNA, and synthetic DNA.

As used herein, the terms "portion", "fragment", "variant", "derivative" and "analog", when referring to a polypeptide include any polypeptide that retains at least some biological activity referred to herein (e.g., inhibition of an interaction such as binding). Polypeptides as described herein may include portion, fragment, variant, or derivative molecules without limitation, as long as the polypeptide still serves its function. Polypeptides or portions thereof of the present invention may include proteolytic fragments, deletion fragments and in particular, or fragments that more easily reach the site of action when delivered to an animal.

Embodiments described herein relate to compositions and methods for inhibiting cancer cell proliferation by activation of ChK1 in the cancer cells. It was found that that activation of Chk1 only (e.g., using constitutively active Chk1, mutant thereof, or polypeptide fragment thereof) but not the entire ATR pathway, is detrimental to cell viability without exogenous DNA damage. The existence of constant S phase "checkpoints" posed by this constitutively active Chk1 can stop cancer cell division and growth and treat cancer.

In some embodiments, the compositions described herein can include exogenous constitutively active Chk1 (SEQ ID NO: 1) or an agent that promotes phosphorylation of endogenous Chk1 (e.g., SEQ ID NO: 2) of the cancer cell.

In other embodiments, the constitutively active Chk1 can include Chk1 that is phosphorylated after administration to or expression in the cancer cell. For example, the constitutively active Chk1 can include an L449R mutant (e.g., SEQ ID NO: 3).

In certain embodiments, the agent can bind to, complex with, and/or act as a competitive inhibitor of the Chk1.

In some embodiments, the agent can include a small molecule or polypeptide that inhibits the interaction of the N-terminal kinase domain and the C-terminal kinase domain of the endogenous Chk1.

The agent can include a polypeptide that has a amino acid sequence with at least 80%, at least 90%, about 95%, about 96%, about 97%, about 98%, about 99% or about 100% sequence identity with amino acids 331-476 of Chk1 (SEQ ID NO: 4) or amino acids 421-476 of Chk1 (SEQ ID NO: 5) and can inhibit the interaction of the N-terminal kinase domain and the C-terminal kinase domain of the endogenous Chk1.

The peptides and/or proteins described herein can also be modified by natural processes, such as posttranslational processing, and/or by chemical modification techniques, which are known in the art. Modifications may occur anywhere in the peptide including the peptide backbone, the amino acid side-chains and the amino or carboxy termini. It will be appreciated that the same type of modification may be present in the same or varying degrees at several sites in a given peptide. Modifications comprise for example, without limitation, acetylation, acylation, addition of acetomidomethyl (Acm) group, ADP-ribosylation, amidation, covalent attachment to fiavin, covalent attachment to a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycosylation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation and ubiquitination (for reference see, Protein-structure and molecular properties, 2nd Ed., T. E. Creighton, W. H. Freeman and Company, New-York, 1993).

Other type of peptide modifications may include for example, amino acid insertion (i.e., addition), deletion and substitution (i.e., replacement), either conservative or non-conservative (e.g., D-amino acids) in the polypeptide sequence where such changes do not substantially alter the overall competitive inhibitor ability of the polypeptide.

Peptides and/or proteins described herein may also include, for example, biologically active mutants, variants, fragments, chimeras, and analogues; fragments encompass amino acid sequences having truncations of one or more amino acids, wherein the truncation may originate from the amino terminus (N-terminus), carboxy terminus (C-terminus), or from the interior of the protein. Analogues of the invention involve an insertion or a substitution of one or more amino acids.

The peptides and/or proteins described herein may be prepared by methods known to those skilled in the art. The peptides and/or proteins may be prepared using recombinant DNA. For example, one preparation can include cultivating a host cell (bacterial or eukaryotic) under conditions which provide for the expression of peptides and/or proteins within the cell.

The purification of the peptides and/or proteins may be done by affinity methods, ion exchange chromatography, size exclusion chromatography, hydrophobicity or any other purification technique typically used for protein purification. The purification step can be performed under non-denaturating conditions. On the other hand, if a denaturating step is required, the protein may be renatured using techniques known in the art.

The peptides and/or proteins can also be in the form of a conjugate protein or drug delivery construct having at least a transport subdomain(s) or moiety(ies) (i.e., transport moieties). The transport moieties can facilitate uptake of the peptides and/or proteins into a mammalian (i.e., human or animal) tissue or cancer cell. The transport moieties can be covalently linked to a peptides and/or proteins. The covalent link can include a peptide bond or a labile bond (e.g., a bond readily cleavable or subject to chemical change in the interior target cell environment). Additionally, the transport moieties can be cross-linked (e.g., chemically cross-linked, UV cross-linked) to the polypeptide.

The transport moieties can be repeated more than once in the peptides and/or proteins. The repetition of a transport moiety may affect (e.g., increase) the uptake of the peptides and/or proteins by a desired cancer cell. The transport moiety may also be located either at the amino-terminal region of an active agent or at its carboxy-terminal region or at both regions.

In some aspects, the transport moiety can include at least one transport peptide sequence that allows the peptides and/or proteins to penetrate into the cell by a receptor-independent mechanism.

Examples of known transport moieties, subdomains and the like are described in, for example, Canadian patent document No. 2,301,157 (conjugates containing homeodomain of antennapedia) as well as in U.S. Pat. Nos. 5,652,122, 5,670,617, 5,674,980, 5,747,641, and 5,804,604, all of which are incorporated herein by reference in their entirety, (conjugates containing amino acids of Tat HIV protein; herpes simplex virus-1 DNA binding protein VP22, a Histidine tag ranging in length from 4 to 30 histidine repeats, or a variation derivative or homologue thereof capable of facilitating uptake of the active cargo moiety by a receptor independent process.

A 16 amino acid region of the third alpha-helix of antennapedia homeodomain has also been shown to enable proteins (made as fusion proteins) to cross cellular membranes (PCT international publication number WO 99/11809 and Canadian application No.: 2,301,157. Similarly, HIV Tat protein was shown to be able to cross cellular membranes.

In addition, the transport moiety(ies) can include polypeptides having a basic amino acid rich region covalently linked to an active agent moiety (e.g., intracellular fragment inhibitor peptide). As used herein, the term "basic amino acid rich region" relates to a region of a protein with a high content of the basic amino acids such as arginine, histidine, asparagine, glutamine, lysine. A "basic amino acid rich region" may have, for example 15% or more of basic amino acid. In some instance, a "basic amino acid rich region" may have less than 15% of basic amino acids and still function as a transport agent region. More preferably, a basic amino acid region will have 30% or more of basic amino acids.

The transport moiety(ies) may further include a proline rich region. As used herein, the term proline rich region refers to a region of a polypeptide with 5% or more (up to 100%) of proline in its sequence. In some instance, a proline rich region may have between 5% and 15% of prolines. Additionally, a proline rich region refers to a region, of a polypeptide containing more prolines than what is generally observed in naturally occurring proteins (e.g., proteins encoded by the human genome). Proline rich regions of the present invention can function as a transport agent region.

In another aspect, the therapeutic polypeptides described herein can be non-covalently linked to a transfection agent. An example of a non-covalently linked polypeptide transfection agent is the Chariot protein delivery system (See U.S. Pat. No. 6,841,535; Morris et al. (1999) J. Biol. Chem. 274(35):24941-24946; and Morris et al. (2001) Nature Biotech. 19:1173-1176), all herein incorporated by reference in their entirety.

In some embodiments, therapeutic agents comprising the therapeutic polypeptides can be provided in a pharmaceutical composition. The pharmaceutical compositions can include a pharmaceutically effective amount of agents described above and a pharmaceutically acceptable diluent or carrier.

The term "pharmaceutically acceptable carrier" "diluents", or "adjuvant" and "physiologically acceptable vehicle" and the like are to be understood as referring to an acceptable carrier or adjuvant that may be administered to a patient, together with an agent of this invention, and which does not destroy the pharmacological activity thereof. Further, as used herein "pharmaceutically acceptable carrier" or "pharmaceutical carrier" are known in the art and include, but are not limited to, 0.01-0.1 M and preferably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

In addition, the term "pharmaceutically effective amount" or "therapeutically effective amount" refers to an amount (dose) effective in treating a patient, having, for example, cancer, such as glioblastoma multiforme. It is also to be understood herein that a "pharmaceutically effective amount" may be interpreted as an amount giving a desired therapeutic effect, either taken into one dose or in any dosage or route or taken alone or in combination with other therapeutic agents.

Determination of a therapeutically effective amount is within the capability of those skilled in the art. The exact formulation, route of administration and dosage can be chosen by the individual physician in view of the patient's condition.

Pharmaceutical compositions of the present invention can be administered in a suitable pharmaceutical carrier by one of several routes which include direct injection, and topical application. Formulations of the compositions will vary according to the route of administration selected (e.g., solution or emulsion).

The therapeutic agents can be delivered to cancer cells in vivo or in vitro by directly contacting the therapeutic polypeptide with specific cell surface receptors, injecting into the cell, or by means of any delivery tag, carrier, vehicle, or technique known and suitable in the art, including a liposome, micelle, fusion tag, antibody, carrier protein, chemical moiety, electroporation, microinjection, viral protein fusions, nanoparticles, and commercial protein delivery reagents. The therapeutic agents can be internalized into the cancer cell, preferably into the cytoplasm, by any passive, facilitated, or active processes.

When the therapeutic agents comprising the therapeutic agents are delivered to a subject, they can be administered by any suitable route, including, for example, orally (e.g., in capsules, suspensions or tablets), systemically, or by parenteral administration. Parenteral administration can include, for example, intramuscular, intravenous, intraarticular, intraarterial, intrathecal, subcutaneous, or intraperitoneal administration. The composition can also be administered orally, transdermally, topically, by inhalation (e.g., intrabronchial, intranasal, oral inhalation or intranasal drops) or rectally. Administration can be local or systemic as indicated.

Both local and systemic administration are contemplated herein. Desirable features of local administration include achieving effective local concentrations of the therapeutic polypeptide as well as avoiding adverse side effects from systemic administration of the therapeutic polypeptide.

In certain embodiments, the therapeutic agent can be delivered to cancer cells by site-specific means. Cell-type-specific delivery can be provided by conjugating a therapeutic agent to a targeting molecule, for example, one that selectively binds to the affected cells. Methods for targeting include conjugates, such as those described in U.S. Pat. No. 5,391,723. Targeting vehicles, such as liposomes, can be used to deliver a compound, for example, by encapsulating the compound in a liposome containing a cell-specific targeting molecule. Methods for targeted delivery of compounds to particular cell types are well-known to those skilled in the art.

In other embodiments, therapeutic polypeptides, such as constitutively active Chk1, constitutively active Chk1, which includes an L449R mutant, or a polypeptide that has a amino acid sequence with at least 80% sequence identity to amino acids 331-476 of Chk1 or amino acids 421-476 of Chk1, can be expressed in cancer cells being treated using gene therapy. The gene therapy can use a vector including a nucleotide encoding the polypeptide mimetics. A "vector" (sometimes referred to as gene delivery or gene transfer "vehicle") refers to a macromolecule or complex of molecules comprising a polynucleotide to be delivered to the cell. The polynucleotide to be delivered may comprise a coding sequence of interest in gene therapy. Vectors include, for example, viral vectors (such as adenoviruses (Ad), adeno-associated viruses (AAV), and retroviruses), liposomes and other lipid-containing complexes, and other macromolecular complexes capable of mediating delivery of a polynucleotide to a target cell.

Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities.

Selectable markers can be positive, negative or bifunctional. Positive selectable markers allow selection for cells carrying the marker, whereas negative selectable markers allow cells carrying the marker to be selectively eliminated. A variety of such marker genes have been described, including bifunctional (i.e., positive/negative) markers (see, e.g., Lupton, S., WO 92/08796, published May 29, 1992; and Lupton, S., WO 94/28143, published Dec. 8, 1994). Such marker genes can provide an added measure of control that can be advantageous in gene therapy contexts. A large variety of such vectors are known in the art and are generally available.

Vectors for use herein include viral vectors, lipid based vectors and other non-viral vectors that are capable of delivering a nucleotide encoding the therapeutic peptides described herein to the target cells. The vector can be a targeted vector, especially a targeted vector that preferentially binds to neurons and. Viral vectors for use in the application can include those that exhibit low toxicity to a target cell and induce production of therapeutically useful quantities of the therapeutic peptide in a cell specific manner.

Examples of viral vectors are those derived from adenovirus (Ad) or adeno-associated virus (AAV). Both human and non-human viral vectors can be used and the recombinant viral vector can be replication-defective in humans. Where the vector is an adenovirus, the vector can comprise a polynucleotide having a promoter operably linked to a gene encoding the therapeutic peptides and is replication-defective in humans.

Other viral vectors that can be used herein include herpes simplex virus (HSV)-based vectors. HSV vectors deleted of one or more immediate early genes (IE) are advantageous because they are generally non-cytotoxic, persist in a state similar to latency in the target cell, and afford efficient target cell transduction. Recombinant HSV vectors can incorporate approximately 30 kb of heterologous nucleic acid.

Retroviruses, such as C-type retroviruses and lentiviruses, might also be used in the application. For example, retroviral vectors may be based on murine leukemia virus (MLV). See, e.g., Hu and Pathak, Pharmacol. Rev. 52:493-511, 2000 and Fong et al., Crit. Rev. Ther. Drug Carrier Syst. 17:1-60, 2000. MLV-based vectors may contain up to 8 kb of heterologous (therapeutic) DNA in place of the viral genes. The heterologous DNA may include a tissue-specific promoter and a nucleic acid encoding the therapeutic peptide. In methods of delivery to neural cells, it may also encode a ligand to a tissue specific receptor.

Additional retroviral vectors that might be used are replication-defective lentivirus-based vectors, including human immunodeficiency (HIV)-based vectors. See, e.g., Vigna and Naldini, J. Gene Med. 5:308-316, 2000 and Miyoshi et al., J. Virol. 72:8150-8157, 1998. Lentiviral vectors are advantageous in that they are capable of infecting both actively dividing and non-dividing cells.

Lentiviral vectors for use in the application may be derived from human and non-human (including SIV) lentiviruses. Examples of lentiviral vectors include nucleic acid sequences required for vector propagation as well as a tissue-specific promoter operably linked to a therapeutic peptide encoding nucleic acid. These former may include the viral LTRs, a primer binding site, a polypurine tract, att sites, and an encapsidation site.

In some aspects, a lentiviral vector can be employed. Lentiviruses have proven capable of transducing different types of CNS neurons (Azzouz et al., (2002) *J. Neurosci.* 22: 10302-12) and may be used in some embodiments because of their large cloning capacity.

A lentiviral vector may be packaged into any lentiviral capsid. The substitution of one particle protein with another from a different virus is referred to as "pseudotyping". The vector capsid may contain viral envelope proteins from other viruses, including murine leukemia virus (MLV) or vesicular stomatitis virus (VSV). The use of the VSV G-protein yields a high vector titer and results in greater stability of the vector virus particles.

Alphavirus-based vectors, such as those made from semliki forest virus (SFV) and sindbis virus (SIN) might also be used in the application. Use of alphaviruses is described in Lundstrom, K., Intervirology 43:247-257, 2000 and Perri et al., Journal of Virology 74:9802-9807, 2000.

Recombinant, replication-defective alphavirus vectors are advantageous because they are capable of high-level heterologous (therapeutic) gene expression, and can infect a wide target cell range. Alphavirus replicons may be targeted to specific cell types by displaying on their virion surface a functional heterologous ligand or binding domain that would allow selective binding to target cells expressing a cognate binding partner. Alphavirus replicons may establish latency, and therefore long-term heterologous nucleic acid expression in a target cell. The replicons may also exhibit transient heterologous nucleic acid expression in the target cell.

In many of the viral vectors compatible with methods of the application, more than one promoter can be included in the vector to allow more than one heterologous gene to be expressed by the vector. Further, the vector can comprise a sequence, which encodes a signal peptide or other moiety, which facilitates expression of the therapeutic peptide from the target cell.

Other nucleotide sequence elements, which facilitate expression of the therapeutic polypeptide and cloning of the vector are further contemplated. For example, the presence of enhancers upstream of the promoter or terminators downstream of the coding region, for example, can facilitate expression.

In accordance with another embodiment, a tissue-specific promoter can be fused to nucleotides encoding the therapeutic polypeptides described herein. By fusing such tissue specific promoter within the adenoviral construct, transgene expression is limited to a particular tissue. The efficacy of gene expression and degree of specificity provided by tissue specific promoters can be determined, using the recombinant adenoviral system of the present application.

In addition to viral vector-based methods, non-viral methods may also be used to introduce a nucleic acid encoding a therapeutic peptide into a target cell. A review of non-viral methods of gene delivery is provided in Nishikawa and Huang, Human Gene Ther. 12:861-870, 2001. An example of a non-viral gene delivery method according to the application employs plasmid DNA to introduce a nucleic acid encoding a therapeutic peptide into a cell. Plasmid-based gene delivery methods are generally known in the art.

Synthetic gene transfer molecules can be designed to form multimolecular aggregates with plasmid DNA. These aggregates can be designed to bind to a target cell. Cationic amphiphiles, including lipopolyamines and cationic lipids, may be used to provide receptor-independent nucleic acid transfer into target cells.

In addition, preformed cationic liposomes or cationic lipids may be mixed with plasmid DNA to generate cell-transfecting complexes. Methods involving cationic lipid formulations are reviewed in Feigner et al., Ann. N.Y. Acad. Sci. 772:126-139, 1995 and Lasic and Templeton, Adv. Drug Delivery Rev. 20:221-266, 1996. For gene delivery, DNA may also be coupled to an amphipathic cationic peptide (Fominaya et al., J. Gene Med. 2:455-464, 2000).

Vectors that encode the expression of the therapeutic peptides can be delivered in vivo to the target cell in the form of an injectable preparation containing pharmaceutically acceptable carrier, such as saline, as necessary. Other pharmaceutical carriers, formulations and dosages can also be used in accordance with the present application.

The vector can be delivered by direct injection at an amount sufficient for the therapeutic polypeptide to be expressed to a degree, which allows for highly effective therapy. By injecting the vector directly into or about the periphery of the cell being treated, it is possible to target the vector transfection rather effectively, and to minimize loss of the recombinant vectors. This type of injection enables local transfection of a desired number of cells, especially at a site of injury, thereby maximizing therapeutic efficacy of gene transfer, and minimizing the possibility of an inflammatory response to viral proteins. Other methods of administering the vector to the target cells can be used and will depend on the specific vector employed.

The therapeutic polypeptide can be expressed for any suitable length of time within the target cell, including transient expression and stable, long-term expression. In one aspect of the application, the nucleic acid encoding the therapeutic peptide will be expressed in therapeutic amounts for a defined length of time effective to inhibit activity and growth of the transfected cancer cells. In another aspect of the application, the nucleic acid encoding the therapeutic peptide will be expressed in therapeutic amounts for a defined length of time effective to inhibit transcription in a targeted cancer cell.

A therapeutic amount is an amount, which is capable of producing a medically desirable result in a treated animal or human. As is well known in the medical arts, dosage for any one animal or human depends on many factors, including the subject's size, body surface area, age, the particular composition to be administered, sex, time and route of administration, general health, and other drugs being administered concurrently. Specific dosages of proteins and nucleic acids can be determined readily determined by one skilled in the art using the experimental methods described below.

Vectors encoding the therapeutic peptides can often be administered less frequently than other types of therapeutics. For example, an effective amount of such a vector can range from about 0.01 mg/kg to about 5 or 10 mg/kg, inclusive; administered daily, weekly, biweekly, monthly or less frequently.

In some embodiments, a therapeutically effective amount of the therapeutic agents described herein (e.g., therapeutic polypeptides, such as constitutively active Chk1, constitutively active Chk1, which includes an L449R mutant, or a polypeptide that has a amino acid sequence with at least 80% sequence identity to amino acids 331-476 of Chk1 or amino acids 421-476 of Chk1) can be administered to a subject for the treatment of a variety of conditions in order to inhibit cell growth in the subject. Such conditions include, without being limited thereto, neoplastic disorder, and in particular all types of solid tumors; skin proliferative diseases (e.g., psoriasis); and a variety of benign hyperplasic disorders.

In one aspect, the neoplastic disorder is cancer. The cancer can include, but is not limited to, carcinomas, such as squamous cell carcinoma, non-small cell carcinoma (e.g., non-small cell lung carcinoma), small cell carcinoma (e.g., small cell lung carcinoma), basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, prostate carcinoma, and squamous cell carcinoma of the neck and head region; sarcomas, such as fibrosarcoma, myxosarcoma, liposarcoma, chondrosarcoma, osteogenic sarcoma, chordosarcoma, angiosarcoma, endotheliosarcoma, lymphangiosarcoma, synoviosarcoma and mesotheliosarcoma; hematologic cancers, such as myelomas, leukemias (e.g., acute myelogenous leukemia, chronic lymphocytic leukemia, granulocytic leukemia, monocytic leukemia, lymphocytic leukemia), lymphomas (e.g., follicular lymphoma, mantle cell lymphoma, diffuse large B-cell lymphoma, malignant lymphoma, plasmocytoma, reticulum cell sarcoma, or Hodgkin's disease), and tumors of the nervous system including glioma, meningoma, medulloblastoma, schwannoma and epidymoma. In certain aspects, the cancer is a pancreatic, breast, lung, colon or glyoblastoma cancer.

In another aspect, the neoplastic disorder is a solid tumor. Exemplary solid tumors include carcinomas, sarcomas, adenomas, and cancers of neuronal origin and if fact to any type of cancer which does not originate from the hematopoeitic cells and in particular concerns: carcinoma, sarcoma, adenoma, hepatocellular carcinoma, hepatocellularcarcinoma, hepatoblastoma, rhabdomyosarcoma, esophageal carcinoma, thyroid carcinoma, ganglioblastoma, fibrosarcoma, myxosarcoma, liposarcoma, cohndrosarcoma, osteogenic sarcoma, chordoma, angiosarcoma, endotheliosarcoma, lymphagiosarcoma, synovioama, Ewing's tumor, leimyosarcoma, rhabdotheliosarcoma, colon carcinoma, pancreatic cancer, breast cancer, ovarian cancer, prostate cancer, squamous cell carcinoma, basal cell carcinoma, adenocarcinoma, renal cell carcinoma, hematoma, bile duct carcinoma, melanoma, choriocarcinoma, seminoma, embryonal carcinoma, Wilms' tumor, cervical cancer, testicular tumor, lung carcinoma, small lung carcinoma, bladder carcinoma, epithelial carcinoma, glioma, astrocyoma, medulloblastoma, craniopharyngioma, ependynoma, pinealoma, retinoblastoma, multiple myeloma, rectal carcinoma, thyroid cancer, head and neck cancer, brain cancer, cancer of the peripheral nervous system, cancer of the central nervous system, neuroblastoma, cancer of the endometrium, as well as metastasis of all the above In some embodiments, therapeutic agents comprising or expressing the therapeutic polypeptides, such as constitutively active Chk1, constitutively active Chk1, which includes an L449R mutant, or a polypeptide that has a amino acid sequence with at least 80% sequence identity to amino acids 331-476 of Chk1 or amino acids 421-476 of Chk1, can be administered to a cancer cell without the administration of an anticancer agent, such as a DNA damaging agent or anti-mitotic agent. Administration of the therapeutic agent to the cancer cells can stop cancer cell division and growth without the use of exogenous DNA damaging agents.

The following example is included to demonstrate different embodiments of the invention. It should be appreciated by those of skill in the art that the techniques disclosed in the examples, which follow represent techniques discovered by the inventor to function well in the practice of the claimed embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the claims.

EXAMPLE 1

Figure 1:
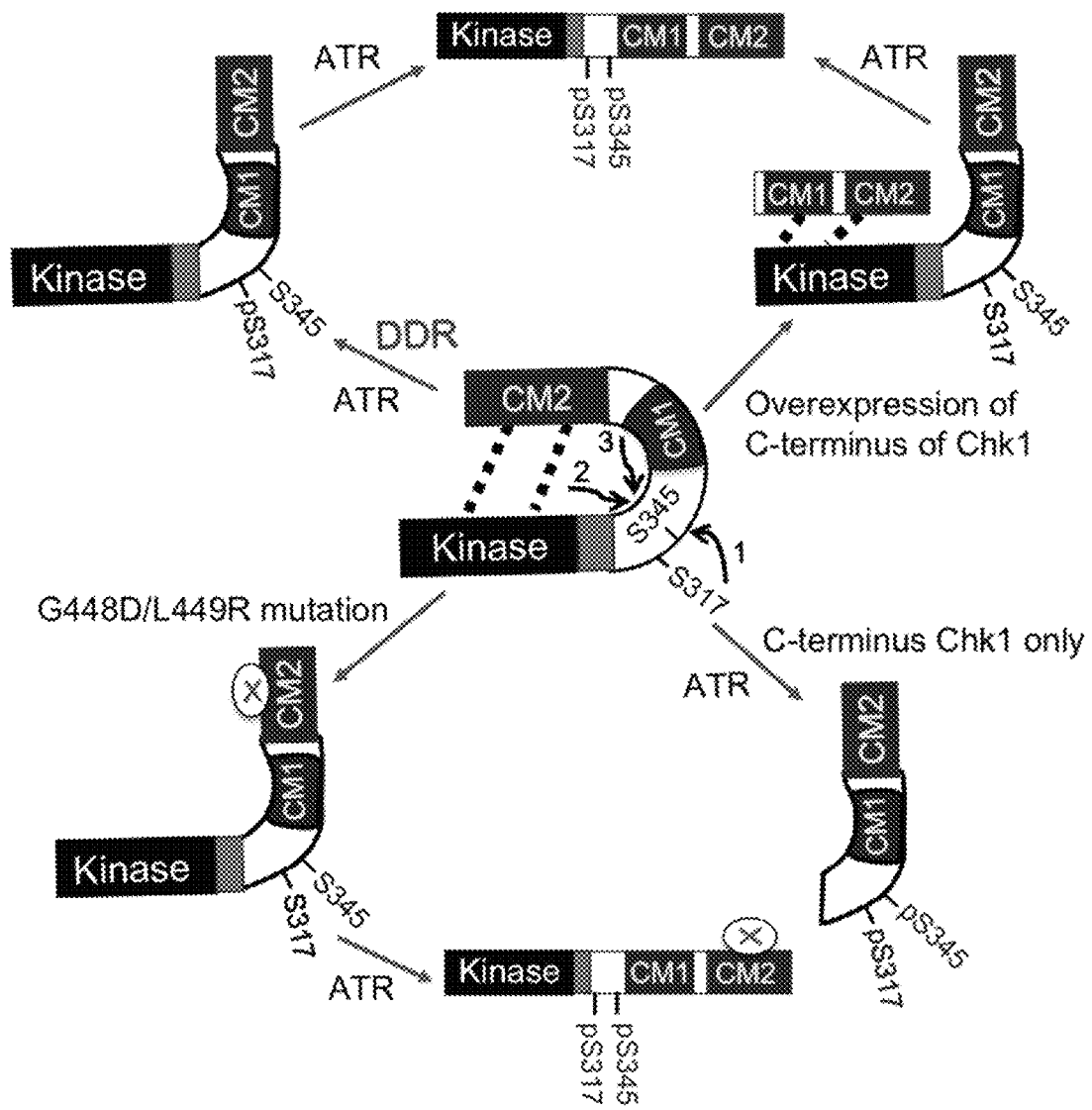
FIG. 1 is a model for Chk1 phosphorylation under different situations. Under DNA damage response (DDR), full phosphorylation of Chk1 requires three steps. 1. Phosphorylation of Ser-317; 2. The relief from the N-terminal kinase domain; and 3. The conformation from CM1 and CM2 domains. Overexpression of the distal C-terminal Chk1, truncation of the N-terminal kinase domain, or mutation of the G448 or L449 residue in the CM2 domain (indicated as 'X') all lead to constitutive phosphorylation of Chk1 in the absence of DNA damage.

In this Example, we show that the Chk1 polypeptide contains a number of critical regulatory mechanisms mediating its own phosphorylation, checkpoint activation, and cell viability. Checkpoint activation requires phosphorylation of Chk1 at both Ser-317 and Ser-345 residues. However, whereas Ser-345 is essential for cell viability, Ser-317 is not. This led to the idea that Ser-345 phosphorylation is the final determinant of checkpoint activation. Our data support this idea by showing that DNA damage-induced Ser-345 phosphorylation of Chk1 is tightly regulated. First, either the phosphate group or N-terminal kinase domain and the involvement of the CM1 and CM2 domains are also required for high-level phosphorylation of Chk1 at 5er-345 (FIG. 1). The C-terminal CM1 and CM2 motifs seem to have dual roles in regulating Chk1 phosphorylation. In the absence of DNA damage, the CM1 and CM2 domains contribute to the inhibitory effect on Chk1 phosphorylation by interacting with the N-terminal kinase domain. On the other hand, the CM1 and CM2 domain contributes to high-level phosphorylation of Chk1 in response to DNA damage, which might be through providing a proper conformation for maximal Ser-345 phosphorylation by ATR.

Previously, Chk1 has been proposed to adopt a "closed" conformation through an intramolecular interaction between the N-terminal kinase domain and the C-terminal regulatory domain. This conformation not only suppresses the catalytic activity of Chk1, but also stabilizes the protein. Data presented in this study added further insights into the fold-back structure of Chk1 and its roles in checkpoint regulation. These new data indicated that under normal circumstances, while the C-terminus of Chk1 masks the kinase domain, the N-terminal kinase domain of Chk1 simultaneously suppresses Chk1 phosphorylation by ATR. These mutual inhibitory effects may provide much safer mechanisms to ensure that no accidental activation of checkpoints, through either the exposure of the catalytic domain or the phosphorylation of the SQ sites of Chk1, will be achieved under normal growth conditions.

It has long been known that inadequate Chk1 phosphorylation leads to checkpoint defects, and consequently loss of cell viability. These new results indicate that cells may have evolved mechanisms to prevent accidental Chk1 phosphorylation when not needed. In agreement with this idea, activation of ATR by expressing the ATR-activating domain of TopBPl or tethering TopBPl or claspin to DNA led to artificial checkpoint activation in the absence of DNA damage. As a result, cells undergo permanent cell-cycle arrest or senescence. However, one potential caveat of these methods is that they activated the entire ATR pathway. In this example, we used the constitutively active Chk1 mutant (L449R) as a model to show that activation of Chk1 only, but not the entire ATR pathway, is detrimental to cell viability without exogenous DNA damage.

The existence of constant S phase "checkpoints" posed by this constitutively active Chk1 mutant is likely to eventually stop cell division and growth. Similarly, mutating the corresponding Leu residue in budding yeast Chk1 (L506) activated check-points in the absence of DNA damage indicating that mechanisms preventing Chk1 from being accidentally phosphorylated might be highly conserved.

An interesting question is how mutation of G448 or L449 leads to constitutive Chk1 phosphorylation at ATR sites. A possible explanation is that these (2 residues sit at the key interface between the N-terminal kinase domain and the C-terminal domain of Chk1. Therefore, mutating one of them fully exposes the Ser-345 site to ATR, leading to its phosphorylation in the absence of DNA damage (FIG. 1).

Material and Methods

Cell Cultures, Transfection, and Cell Proliferation

HEK293T, HeLa, U2-OS, and A549 cells were cultures in Dulbecco's modified Eagle's medium with 10% FBS. Transfection was carried out with either calcium phosphate or Lipofectamine 2000 (Invitrogen). For the cell proliferation assay, HEK293T cells were transfected with GFP, GFP-Chk1 wild type (WT), or the L449R mutant for 48 hours. The cells were reseeded at a density of $1 \times 10^4$ cells per well in 6-well plates and cultured for 8 days. On each day, the number of GFP-positive cells within a colony was counted under fluorescence microscopy.

Plasmid Construction and Mutagenesis

Myc- or GFP-tagged vectors expressing Chk1 WT or mutants were generated using standard PCRs. Point mutations were carried out using the Quick Change mutagenesis kit (Stratagene). Primer information will be provided upon request.

Cell-Cycle Analysis, Immunoblotting, and Antibodies

Cell-cycle analyses and immunoblotting were carried out as previously described. Anti-Chk1 (DCS-1310 and G4) and anti-ATR (N-19) antibodies were from Santa Cruz. Anti-phospho-S317-Chk1, anti-phospho-S345-Chk1, anti-phospho-S1981-ATM, and anti-phospho-S216-Cdc25C were from Cell Signaling. Anti-MCM7 and anti-Cyclin B were from BD Pharmingen. Anti-Cdc25A was from NeoMarkers.

EdU Staining

HeLa Tet/Off cells grown on glass cover slips were transfected with tetracycline-controlled GFP, GFP-Chk1 WT, or the L449R mutant for 24 hours, synchronized at the $G_2/M$ phase with 100 ng/mL nocodazole for 20 hours in the presence of doxycycline, washed twice with 1×PBS, and released into fresh medium without doxycycline. After a 16-hour release from nocodazole, cells were pulse labeled with 10 μmol/L 5-ethynyl-2'-deoxyuridine (EdU), a nucleotide analog, for 20 minutes at 0-, 4-, 8-, and 10-hour time period. Cells were then washed with ice-cold PBS and fixed with 3.7% formaldehyde at room temperature for 10 minutes and followed with the "Click-iT" kit to measure EdU incorporation according to the manufacturer's instruction (Invitrogen).

Results

The Kinase, CM1 or CM2 Domain is not Essential for Human Chk1 Phosphorylation

Figure 2:
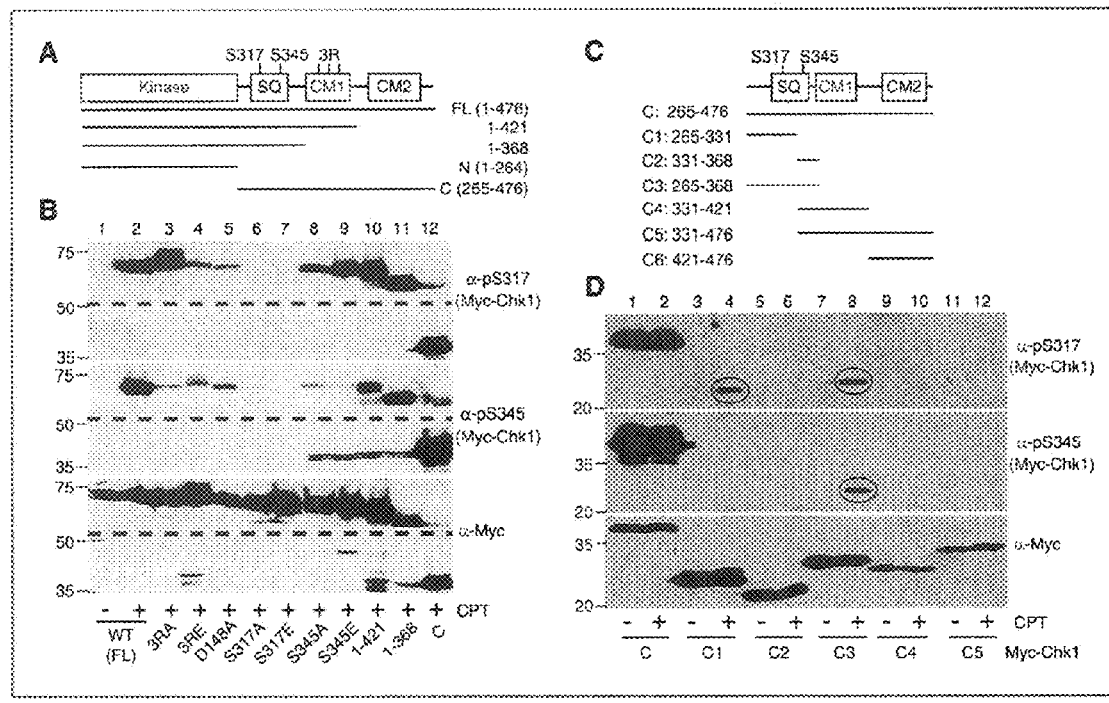
FIG. 2 illustrates Chk1 phosphorylation at ATR sites. A, schematic diagram of human Chk1 and generation of deletion mutations. SQ, Ser/Gln; CM, conserved motif; 3R, Arg 372/376/379; FL, full-length (1-476); N, amino terminus; C. carboxyl terminus. B, HEK293T cells were transfected with Myc-tagged Chk1 WT or mutants for 48 hours, treated or not with 500 nmol/L CPT for 2 hours and immunoblotted with indicated antibodies. 3RA and 3RE are Arg to Ala and Glu mutations, respectively. C, generation of small fragments of the Chk1 C-terminus D, HEK293T cells were transfected with Myc-tagged Chk1 C-terminal fragments for 48 hours, treated or not with 500 nmol/L CPT for 2 hours, and immunoblotted with indicated antibodies. Phosphorylated Chk1 small fragments are illustrated in the oval.

The kinase, CM1 and CM2 domains of Chk1 (FIG. 2A) are highly conserved among different species. However, whether these domains are required for initiating Chk1 phosphorylation at ATR sites is unknown. To address this question, we generated Myc-tagged mutants in which the kinase domain (the C mutant), the CM2 domain (the 1-421 mutant) or the CM1 plus CM2 domain (the 1-368 mutant) of human Chk1 were deleted (FIG. 2A). All these mutants contain the 2 ATR phosphorylation sites, Ser-317 and Ser-345. HEK293T cells expressing these mutants were treated with a DNA-damaging agent, the topoisomerase 1 inhibitor, camptothecin (CPT), and immunoblotted with anti-phospho-Chk1 antibodies. The results showed that deletion of the kinase, CM2 or the CM1 plus CM2 domain did not abolish Chk1 phosphorylation (FIG. 2B, lanes 10-12). These data suggested that none of these 3 conserved domains were essential for Chk1 phosphorylation at ATR sites.

Ser-317 is Required for Phosphorylation at Ser-345

Previous studies reported that mutating the Ser-317 to Ala abolished phosphorylation at the Ser-345 site of Chk1. Here we asked whether the phospho-mimic S317E mutation would induce Chk1 phosphorylation at Ser-345. Consistent with previous publications, the S317A mutant failed to undergo phosphorylation at either the Ser-317 or the Ser-345 site (FIG. 2B, lane 6). However, the S317E mutant also failed to be phosphorylated at the Ser-345 site (FIG. 2B, lane 7), indicating that S317E is not a true phosphomimic mutation or the Ser-31 7 residue is critical for phosphorylation at Ser-345. In contrast, mutating the Ser-345 site to Ala or Glu only moderately reduced Chk1 phosphorylation at the Ser-317 site compared with the Chk1 WT (FIG. 2B, lanes 2).

To further test this idea, we examined protein phosphorylation of more refined mutations of the Chk1 C-terminus expressing one or both phosphorylation sites (C1 to C5 in FIG. 2e) upon CPT treatment. The small fragment C1, which only contains the Ser-317 site, was phosphorylated at the Ser-317 site (FIG. 2D, lanes 3-4). However, the C2, C4, or C5 fragment, which only contains the Ser-345 site, was not phosphorylated at Ser-345 (FIG. 2D, lanes 5-6 and 9-12). Only when the fragment contains both Ser-317 and Ser-345 sites (i.e., the C3 fragment), can phosphorylation at Ser-345 be detected (FIG. 2D, lanes 7-8). These data suggested that either the Ser-317 residue or its phosphorylation is required for phosphorylation at Ser-345, but not the other way around.

Ser-317 Phosphorylation is not Sufficient for Maximal Phosphorylation at Ser-345

We showed that 3 highly conserved Arg residues (R372/376/379) in the CM1 region of Chk1 play an important role in maintaining Chk1 protein conformation. Thus, we asked whether mutating these residues could affect Chk1 phosphorylation upon DNA damage. Our results showed that Chk1 phosphorylation at both Ser 317 and Ser-345 in the 3RE mutant was significantly reduced compared with the Chk1 WT (FIG. 2B, lanes 2 and 4). This seemed to be because of the significantly increased cyto-plasmic localization of this 3RE mutant. On the other hand, the 3RA mutant is located mainly in the nucleus like the WT (data not shown). Interestingly, although the 3RA mutant was highly phosphorylated at the Ser-317 site. Phosphorylation at the Ser-345 site was significantly reduced compared with the Chk1 WT (FIG. 2B. lanes 2-3). We also noticed that the Chk1 (1-421) mutant exhibited more profound reduction in phosphorylation at the Ser-345 site than the Ser-317 site compared with the Chk1 WT (FIG. 2B, lanes 2 and 10). The Chk1 kinase dead (D148A) mutant exhibited reduced phosphorylation at both sites (FIG. 2B, lane 5), probably because this mutant is less stable than the Chk1 WT (FIG. 9A). These results showed that high level phosphorylation at Ser-317 does not necessarily correlate with high-level phosphorylation at Ser-345. Thus, even though the CM1 and CM2 domains are not essential for initiating Chk1 phosphorylation, they seem to contribute to maximal phosphorylation at the Ser-345 site by DNA damage. These data are consistent with yeast Chk1 whose C-terminus contributed to the full activation of Chk1.

Together, these results indicated that phosphorylation at Ser-317 is necessary, but not sufficient, for high level of Chk1 phosphorylation at the Ser-345 site. This is in line with the idea that phosphorylation at the Ser-345 site is the final determinant of full activation of Chk1. Therefore, we focused mainly on Chk1 phosphorylation at the Ser-345 site for the following studies.

ATR-Dependent Constitutive Phosphorylation of the Chk1 C-Terminus

During our analysis, we unexpectedly discovered that the Chk1 C-terminus devoid of the kinase domain was constitutively phosphorylated at both Ser-317 and Ser-345 sites (FIGS. 2D and 2A, lane 1). CPT treatment did not further increase protein phosphorylation compared with the basal state (FIGS. 2D and 2A, lanes 1-2). We also noticed a weak constitutive phosphorylation of the C3 fragment in the absence of DNA damage (FIG. 4A lane 5 and FIG. 3B lane 6), similar to the entire Chk1 C-terminus (FIG. 4B, lane 3). These results suggested that the N-terminal kinase domain suppresses phosphorylation of residues located at the C-terminus of Chk1 in the absence of DNA damage. To understand the biologic implications of this constitutive phosphorylation of the Chk1 C-terminus, we asked whether this Chk1 C-terminus displayed properties similar to those that govern phosphorylation regulation as the full-length (FL) Chk1.

Figure 3:
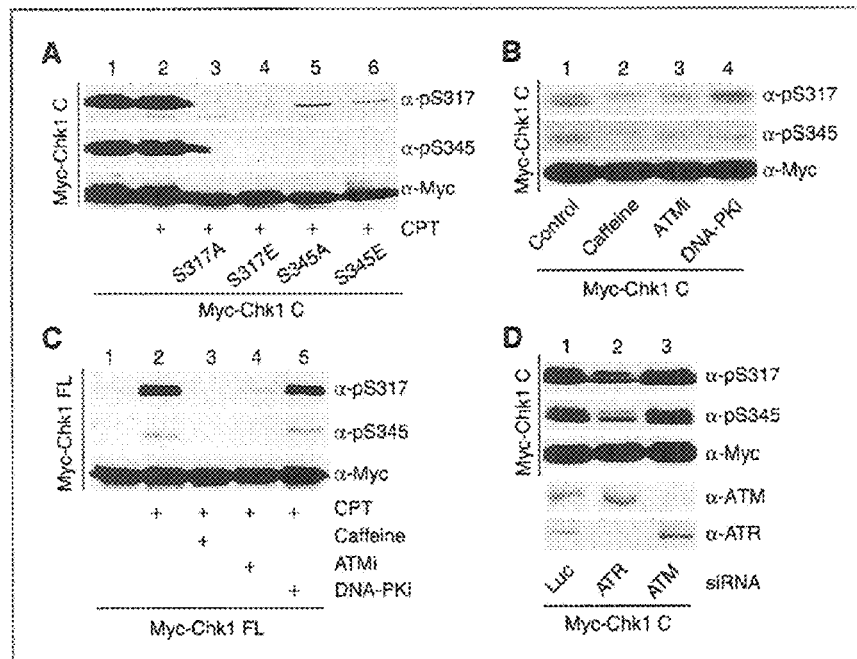
FIG. 3 illustrates constitutive phosphorylation of the Chk1 C-terminus at ATR sites. A, HEK293T cells were transfected with vectors expressing Myc-Chk1 C-terminus with (lanes 3-6) or without (lanes 1-2) mutating Ser-317 or Ser-345 for 48 hours, treated or not with 500 nmol/L CPT for 2 hours and immunoblotted with indicated antibodies. Results for Myc-Chk1 C are shown. B, HEK293T cells were transfected with Myc-Chk1 C for 48 hours, treated with 10 mmol/L caffeine or 1 µmol/L inhibitors against ATM or DNA-PK for 4 hours, and immunoblotted the same as in A. Results of short exposure (~1 sec) for Myc-Chk1 C are shown. C, HEK293T cells were transfected with Myc-Chk1 FL for 48 hours, pretreated with caffeine or other inhibitors for 2 hours followed by 500 nmol/L CPT for an additional 2 hours, and immunoblotted the same as in A. Results for Myc-Chk1 FL are shown. D, HEK293T cells were transfected with siRNAs against luciferase control (Luc), ATR, or ATM for 24 hours, retransfected with Myc-Chk1 C for an additional 48 hours, and immunoblotted the same as in A. Results for Myc-Chk1 C are shown.

First, we observed that the constitutive phosphorylation of this fragment was completely abolished when Ser-317 was mutated to Ala or Glu (FIG. 3A, lanes 3-4). Mutating the Ser-345 to Ala or Glu significantly reduced the constitutive phosphorylation of the Chk1 C-terminus (FIG. 3A, lanes 5-6); however, treating these cells with CPT increased Ser-317 phosphorylation (data not shown). These results suggested that the Chk1 C-terminus undergoes phosphorylation in a way similar to the Chk1 FL protein (FIG. 2A). Second, we asked whether ATR is also responsible for this constitutive phosphorylation of the Chk1 C-terminus. Our results showed that inhibiting ATR, and to a lesser extent, ATM, but not DNA-PK, reduced the levels of phosphorylated proteins of this Chk1 C-terminal fragment (FIG. 3B). In parallel, similar effects were observed on phosphorylation of the Chk1 FL induced by CPT (FIG. 3C). Furthermore, we showed that depletion of ATR, but not ATM, clearly reduced the level of constitutive phosphorylation of the Chk1 C-terminal fragment under normal growth condition (FIG. 3D, lane 2). Owing to the fact that ATM-dependent activation of ATR only occurs in the presence of DNA damage, these results suggested that ATR is the predominant kinase that causes the constitutive phosphorylation of the Chk1 C-terminal fragment in nontreated cells.

Mechanisms Suppressing Chk1 Phosphorylation Under Normal Growth Conditions

Previously, the C-terminus of Chk1 was proposed to form an intramolecular interaction with the N-terminal kinase domain, so that the catalytic activity of the "open" kinase domain of Chk1 is suppressed under normal conditions (FIG. 1). Here we showed that deletion of the N-terminal kinase domain led to constitutive phosphorylation of the C-terminus of Chk1, suggesting that another purpose of this intramolecular interaction might be to suppress Chk1 phosphorylation in the absence of DNA damage.

If this hypothesis is correct, then we would expect that interrupting the interaction between the N-terminal kinase domain and the C-terminus of Chk1 should lead to constitutive phosphorylation of endogenous Chk1 under normal conditions. To address this issue, we overexpressed those small fragments of Chk1 (FIG. 2C) into HEK293T cells and examined phosphorylation of endogenous Chk1. This experimental design was based on the assumption that one or more than one of those exogenous small Chk1 fragments will compete with the C-terminus of endogenous Chk1 for the interaction with the N-terminal kinase domain of the same Chk1 molecule and disrupt the "closed" conformation of Chk1. As a result, the C-terminus of endogenous Chk1 is now exposed to undergo constitutive phosphorylation at ATR sites (FIG. 1). Our results showed that expression of the C5 fragment, and to a lesser extent, the C6 fragment, but not other small fragments, induced phosphorylation of endogenous Chk1 under normal growth conditions (FIG. 4A, lanes 9 and 11). Treatment with a replicative stress, hydroxyurea (HU), only moderately further increased the phosphorylation signal of endogenous Chk1 proteins in the presence of the Chk1 C5 fragment (FIG. 4A, lanes 9-10).

Figure 10A:
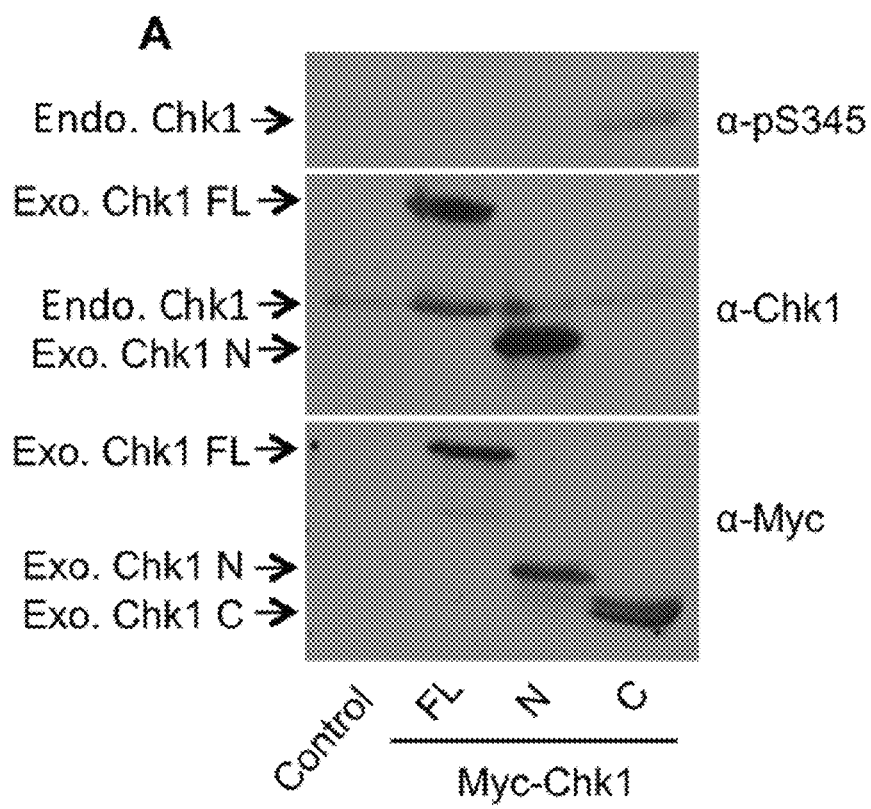
Figure 10B:
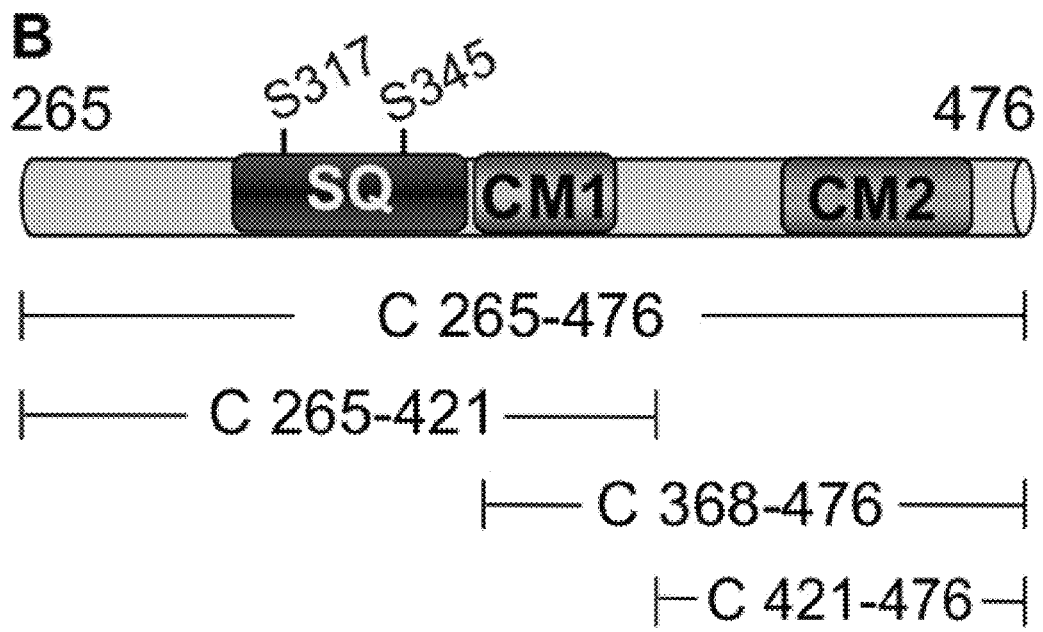
Figure 10C:
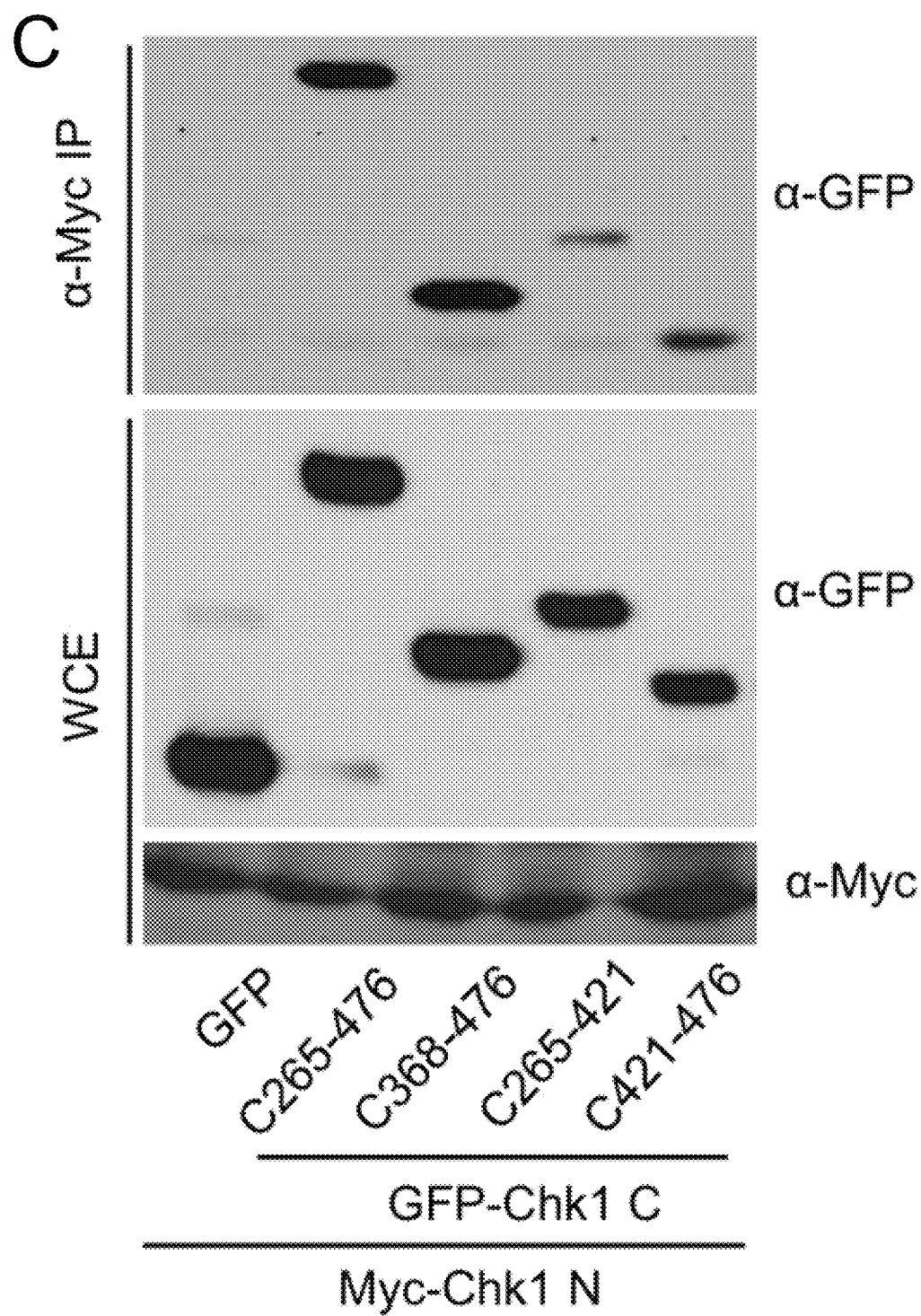

We further showed that overexpression of the C5 fragment and to a lesser extent, the entire C-terminus, induced strong phosphorylation of endogenous Chk1 proteins in another cell line, HeLa (FIG. 4B, lanes 3 and 8), indicating that this is not a cell line-specific effect. On the other hand, the Chk1 FL, the N-terminal kinase domain, or other fragments failed to do so (FIG. 10A). The reason why the C5 fragment, which contains the CM1 and CM2 domains, caused the strongest phosphorylation of endogenous Chk1 is probably because this fragment interacts most strongly with the N-terminal kinase domain (FIG. 10C), thereby providing the maximal interference of the "closed" conformation of endogenous Chk1 (FIG. 1).

If the CM1 and CM2 domains were critical for preventing phosphorylation of Chk1 under normal conditions, then we would expect to identify key residues within these domains, whose mutation should disrupt the intramolecular interaction and lead to constitutive phosphorylation of Chk1 in the absence of DNA damage. To address this issue, we generated GFP-tagged FL Chk1 vectors, in which essentially every residue within the CM1 and CM2 domains was mutated and examined protein phosphorylation with or without CPT treatment. The majority of these point mutations did not show constitutive phosphorylation of Chk1 (data not shown). However, mutating one of 2 residues in the CM2 domain (G448 or L449) led to constitutive phosphorylation of GFP-Chk1 in the absence of DNA damage (FIG. 5, lanes 9 and 11). Phosphorylation of endogenous proteins, including Chk1 and ATM, was not observed in cells expressing these 2 mutants (FIG. 5. endogenous Chk1), indicating the lack of a pan-cellular DNA damage response. CPT treatment moderately increased the phosphorylation signal of these 2 mutants (FIG. 5, lanes 9-12). These data suggested that these 2 residues (G448 and L449) play important roles in suppressing constitutive phosphorylation of Chk1 under normal conditions.

The L449R Mutant Undergoes the Same Regulation as Endogenous Chk1

Figure 6:
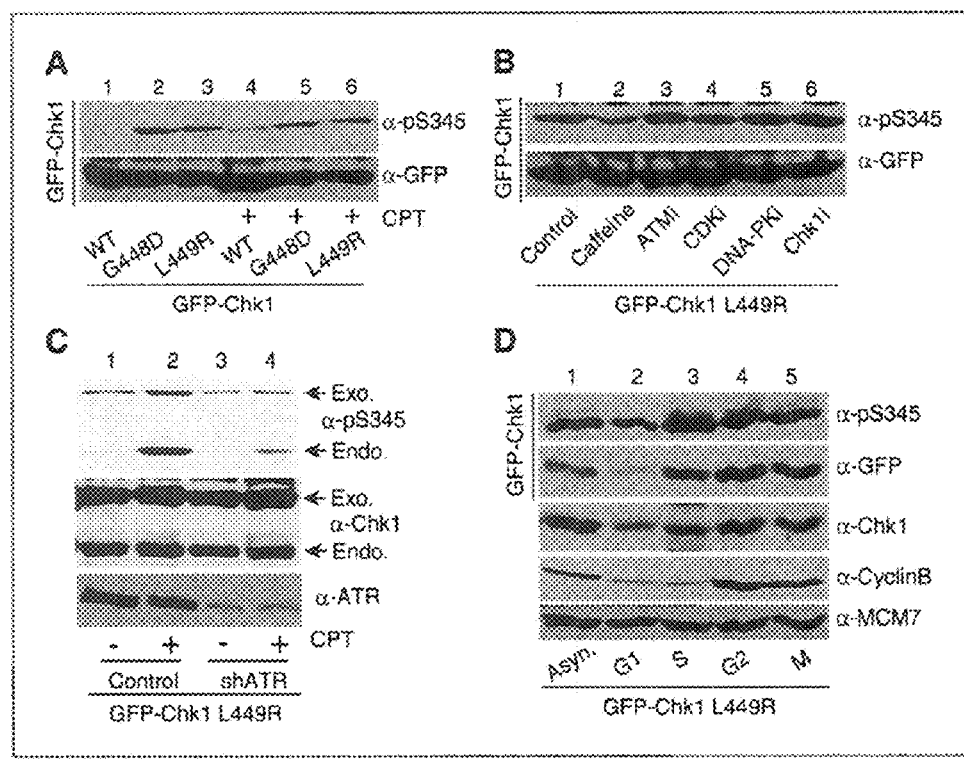
FIG. 6 illustrates constitutive phosphorylation of the Chk1 L449R mutant. A, HeLa cells were transfected with GFP-Chk1 WT, G448D, or L449R mutant for 48 hours, treated or not with 500 nmol/L CPT for 2 hours, and immunoblotted with indicated antibodies. Results for GFP-Chk1 are shown. B. HEK293T cells were transfected with GFP-Chk1 L449R mutant for 48 hours, treated with 10 mmol/L caffeine or 1 μmol/L kinase inhibitors for 4 hours, and immunoblotted as in A. Results for GFP-Chk1 are shown. C, HEK293T cells were cotransfected with GFP-Chk1 L449R and lentivirus vector control or shATR for 72 hours, treated or not with 500 nmol/L CPT for 2 hours, and immunoblotted as in A. D, HeLa cells were transfected with GFP-Chk1 L449R vector for 24 hours, synchronized at $G_2/M$ phase by 100 ng/mL nocodazole treatment for 20 hours, released into different cell-cycle stages, and immunoblotted with indicated antibodies.

To further understand the physiologic relevance of the constitutive phosphorylation of these Chk1 mutants, we first asked whether it is a cell line-specific effect or not. We consistently detected high levels of constitutive phosphorylation of Chk1 mutants in HeLa, U2-OS, A549, or HCT116 cell lines (FIG. 6A HeLa cells, lanes 2-3; data not shown). In contrast, phosphorylation of the Chk1 WT was only detected by CPT treatment (FIG. 6A. lanes 1 and 4). Thus, constitutive phosphorylation of these two Chk1 mutants is not restricted to one system or cell line.

Second, we asked whether this constitutive phosphorylation is also ATR dependent Inhibiting ATR, but not other kinases, reduced the level of constitutive phosphorylation of the Chk1 L449R mutant (FIG. 6B, lane 2). Considering that cells were only treated with caffeine for hours although they had expressed the L449R mutant for days, the reduction in Chk1 phosphorylation is significant. Depletion of ATR significantly reduced phosphorylation of the Chk1 L449R mutant, in a way similar to endogenous Chk1 (FIG. 6C). Together, these data strongly indicated that constitutive phosphorylation of the Chk1 L449R mutant is ATR dependent.

Third, we asked whether the L449R mutant follows a similar cell-cycle-dependent expression pattern as endogenous Chk1 whose expression peaks in the S to $G_2$ phase. The results showed that indeed the level of the GFP-Chk1 L449R mutant was the highest from S to $G_2$ phase, similar to endogenous Chk1 (FIG. 6D, compare the anti-GFP and the anti-Chk1 blots). No phosphorylation was detected for endogenous Chk1 in the absence of DNA damage; however, phosphorylation of the L449R mutant was detected throughout the cell cycle, with the highest in the S phase (FIG. 6D, lane 3 in the anti-pS345 blot). Together, these data suggested that the Chk1 L449R mutant undergoes the same regulation as the endogenous Chk1 protein.

Figure 10D:
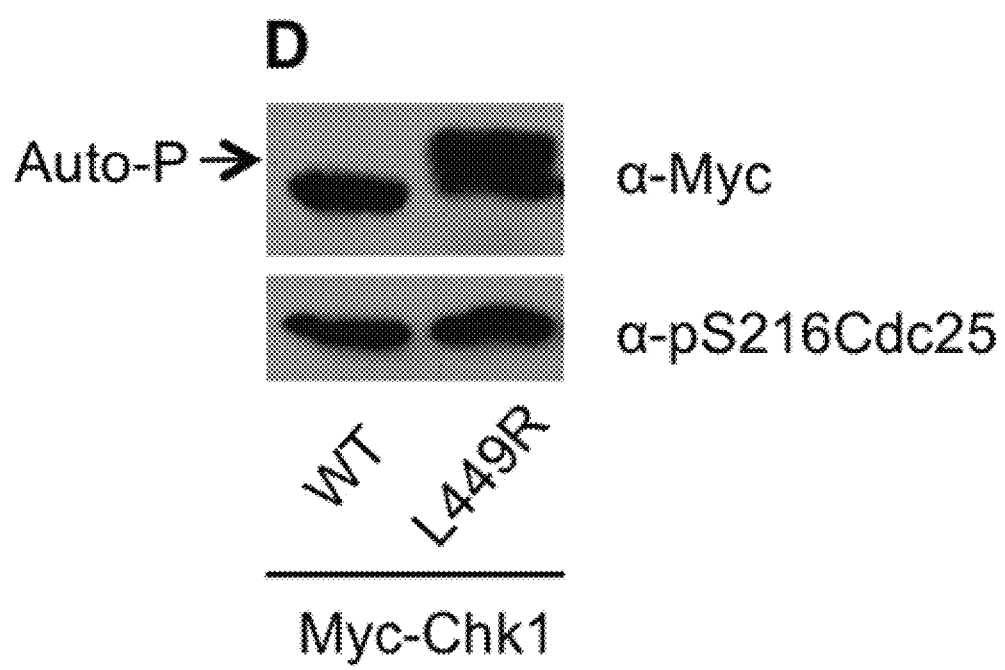

Constitutive Activation of Chk1 in the Absence of DNA Damage Reduces Cell Viability To understand the biologic significance of the constitutive phosphorylation of Chk1, we first asked whether it induced an artificial S-phase checkpoint. To this end, we transfected Tet/Off cells with tetracycline-regulated expression vectors for GFP, GFP-Chk1 WT, or the L449R mutant and examined expression of Cdc25A. Cdc25A is a key Chk1 downstream target that plays a crucial role in regulating both the entry and the progression of S phase. Activation of Chk1 leads to the proteasome-dependent degradation of Cdc25A followed by S-phase progression inhibition. The results showed that the Chk1 WT only slightly reduced the level of Cdc25A compared with GFP alone (FIG. 7A, lanes 3-4), in agreement with our previous report. In contrast, expression of the L449R mutant almost completely blocked Cdc25A expression (FIG. 7A, lane 5), as did the DNA damage agent HU (FIG. 7A, lane 2). Consistent with the reduction of Cdc25A, only HU treatment and the L449R mutant showed Chk1 phosphorylation at Ser345 (FIG. 7A, lanes 2 and 5). In vitro kinase assay showed that the L449R mutant exhibited much stronger autophosphorylation than the Chk1 WT (FIG. 10D). These results showed that the L449R mutant is functionally more active than the Chk1 WT, both in vitro and in vivo.

Subsequently, we tested the effect of the Chk1 L449R mutant on the S-phase progression. HeLa Tet/Off cells blocked at the $G_2$/M phase by nocodazole were released into the cell cycle with concomitant expression of GFP, GFP-Chk1 WT, or the L449R mutant. Our preliminary data showed that a 16-hour release after nocodazole treatment would allow normal HeLa cells to start entering the S phase (data not shown). Thus, we monitored DNA synthesis over a 10-hour period beginning at 16 hours of nocodazole release by measuring the incorporation of EdU, a nucleotide analog (FIG. 11A for experimental design). Fluorescence microscopy revealed that the GFP-Chk1 WT and the L449R mutant were nearly equally expressed at the end of the 16 hours of release (FIG. 11B). Importantly, we found that less cells expressing the GFP-Chk1 L449R were incorporating EdU compared with the GFP-Chk1 WT or the GFP alone (FIG. 7B, 0 hour), indicating a delayed S-phase entry. During the subsequent 10-hour chase period, the number of cells that incorporated EdU in the GFP-Chk1 WT or GFP control group dropped much more significantly than in the L449R group (FIG. 7B, 4-10 hours). This indicated that at a time point when control cells are exiting S phase, GFP-Chk1 L449B-expressing cells remain in the S phase. We also noticed a slightly less reduction in EdU-positive cells in the GFP-Chk1 WT group than the GFP alone (FIG. 7B). This is consistent with the Cdc25A expression profile (FIG. 7A). These data indicated a delayed S-phase entry and prolonged S-phase progression caused by the L449R mutant, and to a much lesser extent, the Chk1 WT compared with the GFP control.

To confirm the prolonged S-phase progression, we analyzed the percentage of late S-phase cells during that 10-hour chase period. Whereas early S-phase cells had a pan-nuclear EdU staining pattern, late S-phase cells exhibited punctuate or more focal EdU staining pattern (FIG. 11C). The results showed that GFP-Chk1 L449R-expressing cells had a significantly lower percentage of late S-phase cells than the GFP-Chk1 WT or the GFP control, especially at later time points (FIG. 7C). Again, the S-phase progression in the GFPChk1 WT was slower than the GFP control (FIG. 7C. more obvious at 0-4 hour). Cell-cycle analyses confirmed that the L449R mutant-expressing cells progressed through S phase much more slowly than GFP control or the Chk1 WT. Together, these data showed that constitutive phosphorylation of Chk1 leads to prolonged S-phase progression.

The cell-cycle analyses showed significantly increased dead cell population for cells expressing the Chk1 L449R mutant, indicating that expression of constitutively active Chk1 is counterproductive to cell viability. To further test this idea, we transfected HEK293T cells with vectors expressing the GFP control, GFP-Chk1 WT or GFP-Chk1 L449R mutant, and counted GFP-positive cell numbers in each clone over 8 days. The results showed that although cells expressing GFP control expanded exponentially, cells expressing GFP-Chk1 WT had a significant delay in expansion; however, no clone expansion was observed for cells expressing the GFP-Chk1 L449R mutant (FIG. 8). Similar results were observed for HeLa, U2-OS, and HCT116 cell lines. These data suggested that constitutive activation of Chk1 suppresses tumor cell growth.

While this invention has been shown and described with references to various embodiments thereof, it will be understood by those skilled in the art that changes in form and details may be made therein without departing from the scope of the invention encompassed by the appended claims. All patents, publications and references cited in the foregoing specification are herein incorporated by reference in their entirety.

Having described the invention the following is claimed:

1. A composition for inhibiting cancer cell proliferation, said composition comprising a vector including a nucleic acid encoding a polypeptide that promotes phosphorylation of endogenous Chk1 of a cancer cell, wherein the polypeptide inhibits cancer cell proliferation in the absence of exogenous DNA damage, wherein when the vector expresses the nucleic acid encoding the polypeptide, the expressed polypeptide consists of a C-terminal fragment of Chk1 having an amino acid sequence with at least 80% sequence identity to amino acids 331-476 of Chk1 or amino acids 421-476 of Chk1 of SEQ ID NO: 2.

2. The composition of claim 1, wherein the composition further comprises a pharmaceutically effective carrier.

3. The composition of claim 1, wherein the polypeptide consists of SEQ ID NO: 4 or SEQ ID NO: 5.

4. A method for inhibiting cancer cell proliferation, comprising: expressing in the cancer cell a therapeutically effective amount of a polypeptide that promotes phosphorylation of endogenous Chk1 of the cancer cell, wherein the expressed polypeptide consists of a C-terminal fragment of Chk1 having an amino acid sequence with at least 90% sequence identity to amino acids 331-476 of Chk1 or amino acids 421-476 of Chk1 of SEQ ID NO: 2.

5. The method of claim 4, wherein the polypeptide consists of SEQ ID NO: 4 or SEQ ID NO: 5.

* * * * *